US009717821B2

(12) United States Patent
Schutte et al.

(10) Patent No.: US 9,717,821 B2
(45) Date of Patent: *Aug. 1, 2017

(54) FORMULATIONS FOR WOUND THERAPY

(75) Inventors: Eliane Schutte, Utrecht (NL); Linda Zuckerman, Seattle, WA (US); Richard Senderoff, Edmonds, WA (US); Glen Martyn, Leicestershire (GB)

(73) Assignee: Mallinckrodt Pharma IP Trading D.A.C. (IE)

( * ) Notice: Subject to any disclaimer, the term of this patent is extended or adjusted under 35 U.S.C. 154(b) by 192 days.

This patent is subject to a terminal disclaimer.

(21) Appl. No.: 14/131,012

(22) PCT Filed: Jul. 6, 2012

(86) PCT No.: PCT/EP2012/063330
§ 371 (c)(1),
(2), (4) Date: Feb. 27, 2014

(87) PCT Pub. No.: WO2013/004838
PCT Pub. Date: Jan. 10, 2013

(65) Prior Publication Data
US 2014/0369991 A1 Dec. 18, 2014

(30) Foreign Application Priority Data
Jul. 6, 2011 (EP) .................... 11172945

(51) Int. Cl.
| A61L 26/00 | (2006.01) |
| A61K 9/16 | (2006.01) |
| A61K 38/36 | (2006.01) |
| A61K 38/48 | (2006.01) |
| A61K 9/00 | (2006.01) |
| A61L 15/44 | (2006.01) |
| A61L 15/64 | (2006.01) |
| A61K 47/10 | (2017.01) |
| A61K 47/26 | (2006.01) |
| A61L 15/28 | (2006.01) |

(52) U.S. Cl.
CPC ........ A61L 26/0066 (2013.01); A61K 9/0014 (2013.01); A61K 9/1617 (2013.01); A61K 9/1623 (2013.01); A61K 38/363 (2013.01); A61K 38/4833 (2013.01); A61K 47/10 (2013.01); A61K 47/26 (2013.01); A61L 15/28 (2013.01); A61L 15/44 (2013.01); A61L 15/64 (2013.01); A61L 26/009 (2013.01); A61L 26/0023 (2013.01); A61L 26/0042 (2013.01); A61L 26/0085 (2013.01); A61L 2300/252 (2013.01); A61L 2300/254 (2013.01); A61L 2300/418 (2013.01); A61L 2400/04 (2013.01); A61L 2430/34 (2013.01)

(58) Field of Classification Search
None
See application file for complete search history.

(56) References Cited

U.S. PATENT DOCUMENTS

| 4,683,142 A | 7/1987 | Zimmermann |
| 4,752,466 A | 6/1988 | Saferstein et al. |
| 6,762,336 B1 | 7/2004 | MacPhee et al. |
| 6,926,908 B2 | 8/2005 | Robinson et al. |
| 7,052,713 B2 | 5/2006 | Stimmeder |
| 7,189,410 B1 | 3/2007 | Drohan et al. |
| 2008/0003272 A1 | 1/2008 | Rapp et al. |
| 2010/0015090 A1 | 1/2010 | Tung et al. |

FOREIGN PATENT DOCUMENTS

| EP | 0059265 | 9/1982 | |
| WO | 9218164 | 10/1992 | |
| WO | 9609814 | 4/1996 | |
| WO | 9618388 | 6/1996 | |
| WO | 9744015 | 11/1997 | |
| WO | 03037303 | 5/2003 | |
| WO | 2004062704 | 7/2004 | |
| WO | 2007122187 | 11/2007 | |
| WO | 2010002435 | 1/2010 | |
| WO | 2010004004 | 1/2010 | |
| WO | WO 2010/002435 | * 1/2010 | ............. A61L 15/42 |
| WO | 2010136588 | 12/2010 | |
| WO | 2010137981 | 12/2010 | |
| WO | 2010142507 | 12/2010 | |

OTHER PUBLICATIONS

Tang et al., Design of Freeze-Drying Processes for Pharmaceuticals: Practical Advice, Pharmaceutical Research, vol. 21, No. 2, Feb. 2004.*

Schiele, Ulrich, "Haemostyptic Preparations on the Basis of Collagen Alone and as Fixed Combination With Fibrin Glue," Clin. Materials, 1992, pp. 169-177, vol. 9, Elsevier Scient Publishers Ltd. England.

Sondeen, Jill L. PhD, et al., "Comparison of 10 Different Hemostatic Dressings in an Aortic Injury," The Journal of Trauma Injury, Infection, and Critical Care, Feb. 2003, pp. 280-285, Lippincott Williams & Wilkins, Inc.

Kheirabadi, Bijan S. PhD, et al. "Development of a Standard Swine Hemorrhage Model for Efficacy Assessment of Topical Hemostatic Agents," The Journal of Trauma Injury, Infection, and Critical Care, Jul. 2011, pp. S139-S146, vol. 71, Issue 1, Supplement, Lippincott Williams & Wilkins, Inc.

(Continued)

Primary Examiner — Suzanne M Noakes
Assistant Examiner — Stephen Chong

(57) ABSTRACT

The present invention relates to novel formulations comprising a dry powder fibrin sealant comprised of a mixture of fibrinogen and/or thrombin, for use in the treatment of wounds or injuries, in particular for use as a topical hemostatic composition or for surgical intervention.

19 Claims, No Drawings

(56) References Cited

OTHER PUBLICATIONS

Kheirabadi, Bijan S. PhD, et al., "Hemostatic Efficacy of Two Advanced Dressings in an Aortic Hemorrhage Model in Swine," The Journal of Trauma Injury, Infection, and Critical Care, 2005, pp. 25-34, vol. 59 No. 1, discussion 34-35, Lippincott Williams & Wilkins, Inc.

Margolis, J., "The Effect of Colloidal Silica on Blood Coagulation," Aust. J. exp. Biol., 1961, pp. 249-258, vol. 39, Children's Medical Research Foundation, Royal Alexandra Hospital for Children, Sydney.

Coller, Barry S., "In Vitro Studies of a Potential Autologous, Semi-artificial Alternative to Platelet Transfusions," J. Clin. Invest., Feb. 1992, pp. 546-555, vol. 89, The American Society for Clinical Investigation, Inc.

* cited by examiner

FORMULATIONS FOR WOUND THERAPY

CROSS-REFERENCE TO RELATED APPLICATIONS

This is the National Phase entry of International Patent Application No. PCT/EP2012/063330, filed Jul. 6, 2012, which claims priority to European Patent Application No. 11172945.5, filed Jul. 6, 2011, both of which are incorporated herein by reference in their entirety.

FIELD OF THE INVENTION

This invention relates to novel formulations comprising a fully biodegradable dry powder fibrin sealant or topical hemostat for use in the treatment of wounds or injuries, in particular for use as an improved topical hemostatic composition which is suitable for treating severe wounds and injuries.

BACKGROUND OF THE INVENTION

New techniques, devices, and drugs for bleeding and/or haemorrhage control are being developed, particularly for severe bleeds. Despite all of the technology currently available, bleeding and haemorrhage control is still a major unresolved problem in emergency medical care. Almost 50% of all deaths in the first 48 hours of hospitalization are related to an inability to adequately control bleeding. Failure to stop bleeding within the first 24 hours is almost always fatal, especially when multiple trauma sites are involved. It is generally accepted that hemostatic products for forward care in a battle zone must control bleeding quickly, be ready to use, simple to apply, have a shelf life at ambient temperatures approaching two years and ideally prevent bacterial growth or viral transmission/reactivation. The product's hemostatic action is time-critical in order to meet both military and civilian needs.

Devices being investigated or used today as external methods of wound treatment range from absorbent pads containing clotting agents, pressure bandages, gauze, tourniquets for extremities, and trauma kits for wounds to the body.

Agents designed to stop external bleeding differ in composition and components but are often designed to help the rapid formation of a clot at the site of application. Clotting products generally contain varying but often high concentrations of materials such as human fibrinogen, thrombin, calcium, factor XIII and/or anti-fibrinolytics. In addition to fibrin, microporous polysaccharide macrobeads, mineral and synthetic zeolites, and chitosan (poly-N-acetyl glucosamine) are also available for use as hemostats. A number of new hemostatic products are available for treating wound trauma, for example, a bandage product using chitosan (deacetylated poly-N-acetyl glucosamine base, HemCon Inc., Tigard, USA), which is a freeze-dried chitosan dressing purportedly designed to optimize the mucoadhesive surface density and structural integrity of the chitosan at the site of the wound. The HemCon™ Chitosan Bandage apparently exerts its hemostatic effects primarily through adhesion to the wound, although there is evidence suggesting it may also enhance platelet function and incorporate red blood cells into the clot it forms on the wound. This bandage has shown improved hemostasis and reduced blood loss in several animal models of arterial haemorrhage, but a marked variability was observed between bandages, including the failure of some due to inadequate adherence to the wound. (See McManus et al, Business Briefing: Emergency Medical Review 2005, at 79). However, it only has a shelf life of 18 months. Another product based on chitosan is the Rapid Deployment Hemostat™ (RDH), (Marine Polymer Technologies, Danvers, USA), which appears to exert its hemostatic effect through red blood cell aggregation, platelet activation, clotting cascade activation and local vasoconstriction. The Rapid Deployment Hemostat™ is an algae-derived dressing composed of poly-N-acetyl-glucosamine. While the original dressing design was effective in reducing minor bleeding, it was necessary to add gauze backing in order to reduce blood loss in swine models of aortic and liver injury. (See McManus et al, Business Briefing: Emergency Medical Review 2005, page 78).

Z-Medica Corporation, Connecticut, USA, market a pressure bandage product (QuikClot®) for use by U.S. troops. This product uses a granular, synthetic mineral zeolite to stop bleeding by adsorbing liquid and promoting clotting. However, QuikClot® generates heat that can cause burns if the bandage isn't applied correctly and the mineral material is not biodegradable and so therefore has to be surgically removed.

Another commonly used hemostatic product is Combat Gauze, a kaolin-coated surgical gauze that is currently used as the standard dressing in the US military.

Nycomed Pharma, Austria, market a matrix of equine collagen coated with human fibrinogen and thrombin, under the trade names of Tachocomb® and Tachosil, which are available for operating room use in many European countries. (See U. Schiele et al, Clin. Materials 9:169-177 (1992)). While these fibrinogen-thrombin dressings do not require the pre-mixing needed by liquid fibrin sealants, their utility for field applications is limited by the common need to pre-moisten the product with saline in order to render it suitably flexible for application to a bleeding sited. Indeed, their field utility has not been observed to date, and it is known that these dressings are also not effective against high pressure, high volume bleeding. (See Sondeen et al. Trauma 54:280-285 (2003)). Another dry fibrinogen/thrombin dressing for treating wounded tissue is disclosed in U.S. Pat. No. 6,762,336, from the American Red Cross (ARC). This particular dressing is composed of a backing material and a plurality of layers, the outer two of which contain fibrinogen (but no thrombin) while the inner layer contains thrombin and calcium chloride (but no fibrinogen). While this dressing has shown success in several animal models of hemorrhage, the bandage is fragile, inflexible, and has a tendency to break apart when handled (See McManus et al, Business Briefing: Emergency Medical Review 2005, page 78; Kheirabadi et al. Trauma 59:25-35 (2005)). The mixing of the fibrinogen and thrombin was found to be very critical on the freeze drying/manufacturing procedure, indicating that complete mixing of the fibrinogen and thrombin active components is essential for full efficacy of the product. This product has not yet been approved for marketing in either the US or the EU.

Other fibrinogen/thrombin-based dressings have also been proposed. For example, U.S. Pat. No. 4,683,142 discloses a resorptive sheet material for closing and healing wounds which consists of a glycoprotein matrix, such as collagen, containing coagulation proteins, such as fibrinogen and thrombin. U.S. Pat. No. 7,189,410 discloses a bandage composed of a backing material having thereon: (i) particles of fibrinogen; (ii) particles of thrombin; and (iii) calcium chloride. US 2008/003272 and WO 00/38752 disclose a fibrin glue in the form of a mixed granulate or granule mixture coated onto a supporting material. EP 0 059 265 discloses a collagen carrier, coated with fibrinogen and thrombin particles. WO 97/44015 discloses a thrombin/ fibrinogen albumin microparticle mixture. WO 2010/002435 discloses a bioresorbable hemostatic pouch comprising fibrinogen or thrombin microparticles as well as glass microparticles in the core.

No perfect solution currently exists for the treatment of excessive or severe bleeding, particularly control of pressure bleeding from arterial or venous bleeding. Heat generation with respect to one type of agent is a major problem. Certain dressing's ability to adhere effectively when applied to deep wounds or wounds of irregular shape creates another major limitation.

Surgical and trauma wounds are the most common types of wounds addressed in the wound-care arena. A further hurdle to overcome when developing products for this field is the deleterious effect of anti-coagulants present in the blood of such surgical patients. Current bandages are made of gauze and are often applied in conjunction with an elastic bandage. They allow the wound to breath but are poor barriers to subsequent contamination. These bandages cannot stop serious bleeding and require the application of pressure in the case of arterial, diffuse or venous bleeding. Many conventional wound sealants fail to present an optimized combination of speed of clotting, effectiveness under high pressure bleeding conditions, and clots that are dynamic over time in response to the needs of the trauma site. Typically, wound sealants are usually used in conjunction with separate wound dressings. Clearly, surgical trauma caused by sharp objects occurs in a clean environment, often as a by-product of the surgical procedure itself. However, trauma wounds not caused in a controlled environment are often intermediate sized, widespread, and dirty wounds with considerable tissue damage are found in road traffic accidents or on the battlefield.

Abrasions are generally caused by scraping of the skin's outer layer; lacerations are jagged, irregular cuts or tears of the skin; punctures are caused by an object piercing the skin layers, creating a small hole; incisions are cuts commonly caused by knives or other sharp objects; and burns cause damage which may vary greatly in depth, size, and severity. Wounds due to firearms can be deep and with substantial tissue destruction. Dismemberment due to trauma requires immediate intervention to stop blood loss from the severed limb.

WO97/44015 only describes a dry powder fibrin sealant based on micro-particles of fibrinogen and thrombin. Further optimised formulations of these microparticle compositions are described in co-pending non-provisional application U.S. Ser. No. 12/636,718.

Accordingly, there remains a need in the art for a solid, ready-for-use (i.e. no reconstitution, mixing, etc.) dressing that can be used to treat wounded tissue, particularly wounded tissue resulting from traumatic injury in the field or in surgery, and/or similar severe bleeding situations. Additionally, there remains a need in the art for a solid and/or flexible or liquid (or viscous liquid), ready-for-use (i.e. no reconstitution, mixing, etc.) hemostatic sealant that can be used to treat wounds having difficult access or requiring space-filling properties. Other advantages of the present invention include improved handling and application in use, the reduced need to employ other hemostatic products and less need for application of additional exogenous microparticles present in the composition according to the invention.

SUMMARY OF THE INVENTION

It is therefore an object of the present invention to provide a composition that can treat wounded tissue, including wounded tissue resulting from a traumatic injury or other severe and/or uncontrolled bleeding conditions, such as surgery. It is further an object of the present invention to provide a method of treating wounded mammalian tissue, particularly human tissue. Other objects, features and advantages of the present invention will be set forth in the detailed description of preferred embodiments that follows, and will in part be apparent from that description and/or may be learned by practise of the present invention. These objects and advantages will be realized and attained by the compositions and methods described in this specification and particularly pointed out in the claims that follow.

In accordance with these and other objects, a first aspect of the present invention is directed to a pharmaceutical composition comprising an absorbable carrier of a biocompatible, biodegradable polymer and dispersed, at least partially through or on said absorbable carrier, microparticles comprising fibrinogen in an amount of from about 0.1-15 mg/cm$^2$ or microparticles comprising thrombin in an amount of from about 0.01 to 500 IU/cm$^2$, wherein the microparticles further comprise a glassy carrier.

In a second aspect of the invention is provided a pharmaceutical composition comprising an absorbable carrier of a biocompatible, biodegradable polymer, wherein dispersed, at least partially through or on said absorbable carrier, is a mixture of microparticles comprising fibrinogen and microparticles comprising thrombin, wherein said first microparticles comprise fibrinogen in an amount of from about 0.1-15 mg/cm$^2$ and said second microparticles comprise thrombin in an amount of from about 0.01 to 500 IU/cm$^2$, wherein either or both said first and second microparticles further comprise a glassy carrier.

In a third aspect of the invention is provided a method of treating a wound or reducing bleeding at a haemorrhaging site, comprising administering to the wound or haemorrhaging site a pharmaceutical composition comprising an absorbable carrier of a biocompatible, biodegradable polymer and dispersed, at least partially through or on said absorbable carrier, microparticles comprising fibrinogen in an amount of from about 0.1-15 mg/cm$^2$ and/or microparticles comprising thrombin in an amount of from about 0.01 to 500 IU/cm$^2$, wherein the microparticles further comprise a glassy carrier.

In a fourth aspect of the invention is provided a method of treating a wound or reducing bleeding at a haemorrhaging site, comprising administering to the wound or haemorrhaging site a pharmaceutical composition comprising an absorbable carrier of a biocompatible, biodegradable polymer and dispersed, at least partially through or on said absorbable carrier, microparticles comprising fibrinogen in an amount of from about 0.1-15 mg/cm$^2$ and/or microparticles comprising thrombin in an amount of from about 0.01 to 500 IU/cm$^2$, wherein the microparticles further comprise a glassy carrier, wherein said treatment results in a time to hemostasis of less than about 10 minutes when administered to a wound which exhibits a bleeding rate of greater than about 30 grams/minute.

In a fifth aspect of the invention is provided the use of an absorbable carrier consisting essentially of a biocompatible, biodegradable polymer selected from a cellulose, polyurethane, gelatin or collagen, such as a collagen-sponge, or a chitosan, and a sufficient amount of amorphous fibrinogen or a sufficient amount of amorphous thrombin, for the preparation of a product for tissue sealing or hemostasis.

In a sixth aspect of the invention is provided a method of making a pharmaceutical composition comprising: (i) suspending in a vehicle in which they are not soluble, microparticles comprising fibrinogen or microparticles comprising thrombin, which microparticles further comprise a glassy carrier, (ii) applying the resulting suspension to an absorbable carrier; and (iii) optionally removing the vehicle.

In a seventh aspect of the invention is provided a method of treating a wound or reducing bleeding at a haemorrhaging site, comprising administering to the wound or haemorrhaging site a pharmaceutical composition comprising an absorbable carrier of a biocompatible, biodegradable polymer and dispersed, at least partially through or on said absorbable carrier, microparticles comprising fibrinogen in an amount of from about 0.1-15 mg/cm$^2$ or microparticles comprising thrombin in an amount of from about 0.01 to 500 IU/cm$^2$, wherein the microparticles further comprise a glassy carrier.

In an eighth aspect of the invention is provided a method of treating a wound or reducing bleeding at a haemorrhaging site, comprising administering to the wound or haemorrhaging site a pharmaceutical composition comprising an absorbable carrier of a biocompatible, biodegradable polymer and dispersed, at least partially through or on said absorbable carrier, microparticles comprising fibrinogen in an amount of from about 0.1-15 mg/cm$^2$ or microparticles comprising thrombin in an amount of from about 0.01 to 500 IU/cm$^2$, preferably a mixture of both, wherein the microparticles further comprise a glassy carrier, and wherein said treatment results in a time to hemostasis of less than about 10 minutes when administered to a wound which exhibits a bleeding rate of greater than about 30 grams/minute.

In a ninth aspect of the invention is provided a pharmaceutical composition comprising an absorbable carrier of a biocompatible, biodegradable polymer, and dispersed at least partially through, in or on said absorbable carrier, a mixture of first microparticles that comprise fibrinogen and second microparticles that comprise thrombin, optionally wherein either or both first and second microparticles further comprise a glassy carrier.

In a further aspect of the present invention is a pharmaceutical composition comprising an absorbable carrier of a biocompatible, biodegradable polymer, and dispersed at least partially through, in or on said absorbable carrier, microparticles that comprise fibrinogen or microparticles that comprise thrombin, optionally wherein the microparticles further comprise a glassy carrier.

In another aspect of the invention is a pharmaceutical composition comprising an absorbable carrier of a biocompatible, biodegradable polymer, and dispersed at least partially through, in or on said absorbable carrier, a mixture of first microparticles that comprise fibrinogen and second microparticles that comprise thrombin, optionally wherein either or both first and second microparticles is of the general type described in WO97/44105, and further optimised formulations of these microparticle compositions as described in co-pending application U.S. Ser. No. 12/636,718, both patents of which are herein incorporated by reference. Thus, the first and second microparticles are suitably prepared by spray-drying as separate products, fibrinogen with trehalose and thrombin with trehalose. Each product has a predominant particle size of up to 50 µm in diameter. The spray-dried fibrinogen and thrombin microparticle powders are non-reactive in the dried state, allowing them to be blended together and applied directly; there is no need for physical separation of thrombin and fibrinogen components by layering or mixing prior to or during administration. The fibrin sealant, a blend of these components, has been demonstrated to be an easy-to-use, stable and efficacious topical hemostat. The product can be used immediately, without reconstitution. On contact with aqueous fluid such as blood, the exposed and/or dissolved active thrombin converts the exposed and/or dissolved fibrinogen into insoluble fibrin polymers.

These microparticle blends may optionally additionally comprise a biocompatible, water-absorbent, water-swellable additive material, or a water-soluble additive material or a biocompatible, water-absorbent, silica additive material, as described in WO 2010/136588, herein incorporated by reference. The additive material can act as a carrier or diluent, may enhance powder flow and wettability and also may have the effect of increasing absorbance of fluid of the bleeding wound, thereby decreasing the local tissue fluid and hence increasing the relative concentration of clotting factors in the wound. By this, the effectiveness of the fibrin sealant is increased.

In a further aspect of the invention is a pharmaceutical composition, optionally in the format of a solid dressing, for treating wounded tissue in a patient comprising fibrinogen and thrombin, wherein the fibrinogen is present in an amount of from about 0.1-15 mg/cm$^2$, preferably about 0.5 to 5 mg/cm$^2$, and thrombin is present in an amount of from about 0.01 to 500 IU/cm$^2$, preferably about 0.1 to 50 IU/cm$^2$.

In yet a further aspect of the invention is a pharmaceutical composition, optionally in the format of a solid dressing, for treating wounded tissue in a patient comprising fibrinogen and thrombin, wherein the fibrinogen is present an amount of from about 0.1-15 mg/cm$^2$, preferably about 0.5 to 5 mg/cm$^2$, and thrombin is present in an amount of from about 0.01 to 500 IU/cm$^2$, preferably about 0.1 to 50 IU/cm$^2$ with regard to the surface area of the wound facing side of the dressing.

It is to be understood that the foregoing general description and the following detailed description of preferred embodiments are exemplary and explanatory only and are intended to provide further explanation, but not limitation, of the invention as claimed herein.

DETAILED DESCRIPTION

Unless defined otherwise, all technical and scientific terms used herein have the same meaning as is commonly understood by one of skill in the art to which this invention belongs. All patents and publications mentioned herein are incorporated by reference.

As used herein, use of a singular article such as "a," "an," and "the" is not intended to excluded pluralities of the article's object unless the context clearly and unambiguously dictates otherwise.

"Patient" as used herein refers to human or animal individuals in need of medical care and/or treatment.

"Wound" as used herein refers to any damage to any tissue of a patient which results in the loss of blood from the circulatory system and/or any other fluid from the patient's body. The damage may have been caused by any agent or source, including traumatic injury, infection or surgical intervention. A wound may be in a soft tissue, such as an organ, or in hard tissue, such as bone. The tissue may be an internal tissue, such as an organ or blood vessel, or an external tissue, such as the skin. The loss of blood may be internal, such as from a ruptured organ, or external, such as from a laceration.

"Resorbable material", "absorbable carrier" and "biocompatible, biodegradable polymer" as used herein, refers to such a material that is broken down spontaneously and/or by the body into components which are degraded or eliminated without causing any significant metabolic disturbance and in such a manner as not to interfere significantly with wound healing and/or tissue regeneration.

"Suitable" as used herein is intended to mean that a material does not adversely affect the stability of the compositions of the invention or any component thereof.

"Release agent" as used herein refers to a compound or mixture of compounds that facilitates removal of a composition of the invention from a manufacturing mould.

"Binding agent" or "binder" as used herein refers to a compound or mixture of compounds that improves the adherence and/or cohesion of the microparticle components to the carrier or matrix material of the compositions of the invention.

"Filler" as used herein refers to a compound or mixture of compounds that provide bulk and/or porosity to the composition of the invention.

"Solid" as used herein is intended to mean that the composition of the invention will not substantially change in shape or form when placed on a rigid surface and then left to stand at 25° C. for 24 hours, and/or is not a liquid at 25° C.

According to Kheirabadi et al. (J. trauma, Injury, Infection and Critical Care; 71: No 1, July Supplement 2011), the ideal hemostatic dressing for tactical applications demonstrates at least one or preferably all of the following characteristics: (a), is approved by the FDA; (b), stops severe arterial and/or venous bleeding in less than or equal to two minutes; (c), has no toxicity or side effects; (d), causes no pain or thermal injury, (e), poses no risk to medics; (f) is ready to use and requires little or no training; (g), is durable and lightweight; (h), is flexible enough to fit complex wounds and is easily removed without leaving residues; (i), is stable and functional at extreme temperatures (−10° C. to +40° C.) for at least two weeks; (j), is practical and easy to use under austere conditions (low visibility, rain, wind, etc.); (k), has a long shelf-life, preferably greater than 2 years; (l), is effective on junctional wounds not amenable without tourniquet; (m), is inexpensive and cost-effective, and; (n) is biodegradable and bioabsorbable. The applicants believe that embodiments of the present invention meet most if not all of the above criteria.

In a first embodiment of the invention is provided a pharmaceutical composition comprising an absorbable carrier of a biocompatible, biodegradable polymer, and dispersed at least partially through, in or on said absorbable carrier, a mixture of first microparticles that comprise fibrinogen and/or second microparticles that comprise thrombin, optionally wherein either or both first and second microparticles further comprise a glassy carrier.

In a second embodiment of the invention is provided a pharmaceutical composition comprising an absorbable carrier of a biocompatible, biodegradable polymer, and dispersed at least partially through, in or on said absorbable carrier, a mixture of first microparticles that comprise fibrinogen and/or second microparticles that comprise thrombin, optionally wherein either or both first and second microparticles further comprise a glassy carrier, wherein the glassy carrier of the first microparticles and/or second microparticles comprises trehalose.

In a third embodiment of the invention is provided a pharmaceutical composition comprising an absorbable carrier of a biocompatible, biodegradable polymer, and dispersed at least partially through, in or on said absorbable carrier, a mixture of first microparticles that comprise fibrinogen and/or second microparticles that comprise thrombin, optionally wherein either or both first and second microparticles further comprise a glassy carrier, and wherein the microparticles are dispersed and/or fixed through, in or on said absorbable carrier.

In a fourth embodiment of the invention is provided a pharmaceutical composition comprising an absorbable carrier of a biocompatible, biodegradable polymer, and dispersed at least partially through, in or on said absorbable carrier, a mixture of first microparticles that comprise fibrinogen and/or second microparticles that comprise thrombin, optionally wherein either or both first and second microparticles further comprise a glassy carrier, and wherein the microparticles are dispersed and/or fixed substantially homogeneously through, in or on said absorbable carrier.

In a fifth embodiment of the invention is provided a pharmaceutical composition comprising an absorbable carrier of a biocompatible, biodegradable polymer, and dispersed at least partially through, in or on said absorbable carrier, a mixture of first microparticles that comprise fibrinogen and/or second microparticles that comprise thrombin, optionally wherein either or both first and/or second microparticles further comprise a glassy carrier, wherein fibrinogen is present in an amount of from about 0.1-15 mg/cm$^2$, preferably about 0.5 to 5 mg/cm$^2$, and thrombin is present in an amount of from about 0.01 to 500 IU/cm$^2$, preferably about 0.1 to 50 IU/cm$^2$. Alternatively, for compositions in a form with three-dimensions (such as a pad, foam and the like where content may be expressed in terms of volume), the fibrinogen is present in an amount of from about 0.1-15 mg/cm$^3$, preferably about 0.5 to 5 mg/cm$^3$, and thrombin is present in an amount of from about 0.01 to 500 IU/cm$^3$, preferably about 0.1 to 50 IU/cm$^3$.

In a sixth embodiment of the invention is provided a pharmaceutical composition comprising an absorbable carrier of a biocompatible, biodegradable polymer, and dispersed at least partially through, in or on said absorbable carrier, a mixture of first microparticles that comprise fibrinogen and/or second microparticles that comprise thrombin, optionally wherein either or both first and/or second microparticles further comprise a glassy carrier, wherein the carrier is flexible and/or porous, and optionally further comprises a plasticizer and/or viscosifying agent.

In a seventh embodiment of the invention is provided a pharmaceutical composition comprising an absorbable carrier of a biocompatible, biodegradable polymer, and dispersed at least partially through, in or on said absorbable carrier, a mixture of first microparticles that comprise fibrinogen and/or second microparticles that comprise thrombin, optionally wherein either or both first and/or second microparticles further comprise a glassy carrier, and wherein the mixture of first and/or second microparticles constitute a layer on one or more surfaces of the absorbable carrier.

In an eighth embodiment of the invention is provided a pharmaceutical composition comprising an absorbable carrier of a biocompatible, biodegradable polymer, and dispersed at least partially through, in or on said absorbable carrier, a mixture of first microparticles that comprise fibrinogen and/or second microparticles that comprise thrombin, optionally wherein either or both first and/or second microparticles further comprise a glassy carrier, and wherein the mixture of first and/or second microparticles constitute a hemostatic layer on one or more surfaces of the absorbable carrier, and optionally wherein the pharmaceutical composition further comprises one or more support layers (e.g. a backing material or an internal support material) and/or release layers.

In an ninth embodiment of the invention is provided a method for treating wounded tissue in a patient, comprising applying a pharmaceutical composition according to the present invention to wounded tissue, and applying sufficient pressure to the composition for a sufficient time for enough fibrin to form to reduce the loss of blood and/or other fluid from the wound For example, the duration of pressure application may be from about 30 seconds to about 10 minutes.

In an tenth embodiment of the invention is provided a method of forming a pharmaceutical composition of the invention, formed or cast as a single piece, preferably wherein a mixture of microparticles is substantially homogeneous throughout, optionally wherein the composition further contains a binding agent to facilitate or improve the adherence of the microparticles to one another and/or to any support layer(s) and/or the absorbable carrier or matrix and/or the tissue. Illustrative examples of suitable binding agents include, but are not limited to, sucrose, mannitol, sorbitol, gelatin, hyaluron and its derivatives, such as hyaluronic acid, maltose, povidone, starch, chitosan and its derivatives, and cellulose derivatives, such as carboxymethylcellulose, hydroxypropylcellulose, as well as mixtures of two or more thereof. The mixture of first and second microparticles comprising fibrinogen and thrombin may also optionally contain one or more suitable fillers, such as sucrose, lactose, maltose, silk, fibrin, collagen, albumin, hyaluronate and its derivatives, such as hyaluronic acid, polysorbates (Tween™), chitin, chitosan and its derivatives, such as NOCC-chitosan, alginic acid and salts thereof, cellulose and derivatives thereof, proteoglycans, glycolic acid polymers, lactic acid polymers, glycolic acid/lactic acid co-polymers, and mixtures of two or more thereof. The mixture of first and second microparticles comprising fibrinogen and thrombin may also optionally contain one or more suitable solubilizing agents, such as sucrose, dextrose, mannose, trehalose, mannitol, sorbitol, albumin, hyaluron and its derivatives, such as hyaluronic acid, polysorbate (Tween™), sorbitan (SPAN™) and mixtures of two or more thereof.

In an eleventh embodiment of the invention is provided a method of forming a pharmaceutical composition of the invention, formed or cast as a single piece, preferably wherein a mixture of microparticles is substantially homogeneous throughout, optionally wherein the composition further contains a suitable source of calcium ions, such as calcium chloride, and/or a fibrin cross-linker, such as a transaminase (e.g. Factor XIII/XIIIa) or glutaraldehyde.

In a twelfth embodiment of the invention, the pharmaceutical composition may optionally further comprise one or more support layers. As used herein, a "support layer" refers to a material that sustains or enhances the structural integrity of the composition and/or the fibrin clot formed when such a composition is applied to wound. In certain embodiments of the present invention, the support layer comprises a backing material on the side of the pharmaceutical composition opposite the side to be applied to wounded tissue. Such a backing material may be affixed with a physiologically-acceptable adhesive or may be self-adhesive. The backing material may comprise one or more resorbable materials or one or more non-resorbable materials, or mixtures thereof. Preferably, the backing material is a single resorbable material. Any suitable resorbable material known and available to those skilled in the art may be employed in the present invention. For example, the resorbable material may be a proteinaceous substance, such as silk, fibrin, keratin, collagen and/or gelatin. Alternatively, the resorbable material may be a carbohydrate substance, such as alginates, hyaluronan and its derivatives, such as hyaluronic acid, sodium hyaluronate, chitin, cellulose, proteoglycans (e.g. poly-N-acetyl glucosamine), lactic acid polymers, glycolic acid polymers, or glycolic acid/lactic acid co-polymers. The resorbable material may also comprise a mixture of proteinaceous substances or a mixture of carbohydrate substances or a mixture of both proteinaceous substances and carbohydrate substances. Suitable examples of particularly preferred resorbable materials include, but are not limited to, the materials sold under the trade names DEXON™ (a glycolic acid polymer) and VICRYL™ (a glycolic acid/lactic acid copolymer). Any suitable non-resorbable material known and available to those skilled in the art may be employed as the backing material, examples of which include, but are not limited to, paper and paper products, latex, plastics, cotton, silicone polymers, gauze and the like.

In a thirteenth embodiment of the invention is provided a method of forming a pharmaceutical composition of the invention, formed or cast as a single piece using a mould, wherein the composition may also optionally further comprise a release layer. As used herein, a "release layer" refers to a layer containing one or more agents ("release agents") which promote or allow removal of the pharmaceutical composition from a mould in which it has been manufactured. A preferred such agent is sucrose, but other suitable release agents include gelatin, mannitol, sorbitol, hyaluron and its derivatives, such as hyaluronic acid, and glucose. Alternatively, such one or more release agents may be contained in the hemostatic layer of microparticles, if presented in such a configuration. The various layers of the inventive compositions may be affixed to one another by any suitable means known and available to those skilled in the art. For example, a physiologically-acceptable adhesive may be applied to a backing material (when present), and the pharmaceutical composition subsequently affixed thereto.

In a fourteenth embodiment of the invention is provided a pharmaceutical composition comprising an absorbable carrier of a biocompatible, biodegradable polymer, and dispersed at least partially through, in or on said absorbable carrier, microparticles that comprise fibrinogen or microparticles that comprise thrombin, optionally wherein either or both of the microparticles further comprise a glassy carrier. Preferably, fibrinogen is present in an amount of from about 0.1-15 mg/cm$^2$ or about 0.5 to 5 mg/cm$^2$ and thrombin is present in an amount of from about 0.01 to 500 IU/cm$^2$, or about 0.1 to 50 IU/cm$^2$. More preferably, the microparticles are present as a mixture of microparticles that comprise fibrinogen and microparticles that comprise thrombin.

In certain embodiments of the present invention, the physiologically-acceptable adhesive has a shear strength and/or structure such that the backing material can be separated from the fibrin clot formed by or within a pharmaceutical composition according to the invention, after its application to wounded tissue. In other embodiments, the physiologically-acceptable adhesive has a shear strength and/or structure such that the backing material cannot be separated from the composition after said application.

During use of a composition according to the invention, the fibrinogen and the thrombin are preferably activated at the time of application to the wounded tissue by the endogenous fluids of the patient escaping from the hemorrhaging wound.

In a fifteenth embodiment of the present invention, the pharmaceutical composition may also contain one or more bioactives, such as growth factors, polyclonal and monoclonal antibodies, drugs, and other compounds including, but not limited to, the following: fibrinolysis inhibitors, such as aprotonin, tranexamic acid and epsilon-amino-caproic acid; antibiotics, such as tetracycline and metronidazole, ciprofloxacin and amoxicillin; anticoagulants, such as activated protein C, prostaglandins (particularly (PGI$_2$), leukotrienes, heparin, ADPase, prostacyclins, antithrombin III, and plasminogen activator; steroids, such as dexamethasone, inhibitors of prostacyclin, prostaglandins, leukotrienes and/or kinins to inhibit inflammation; cardiovascular drugs, such as calcium channel blockers, vasodilators and vasoconstrictors; local anesthetics such as bupivacaine; and antiproliferative/antitumor drugs such as 5-fluorouracil (5-FU), taxol and/or taxotere; anti-virals, such as gancyclovir, zidovudine, amantidine, trifluridine, acyclovir, vidarabine, ribaravin, dideoxyuridine and antibodies to viral components; mammalian gene products; cytokines, such as alpha- or beta-tumour necrosis factor, alpha- or beta- or gamma-Interferon, and interleukins; colony stimulating factors; erythropoietin; antifungals, such as diflucan, ketaconazole and nystatin; antiparasitic gents, such as pentamidine; anti-inflammatory agents, such as alpha-1-anti-trypsin and alpha-1-antichymotrypsin; anaesthetics, such as bupivacaine; analgesics; antiseptics; hormones; vitamins and other nutritional supplements; glycoproteins; fibronectin; peptides and proteins; carbohydrates (both simple and/or complex); proteoglycans; antiangiogenins; antigens; lipids or liposomes; oligonucleotides (sense and/or anti-sense DNA and/or RNA); and gene therapy reagents. In other embodiments of the present invention, the backing layer, if present, may contain one or more bioactives.

In a sixteenth embodiment of the present invention, the pharmaceutical composition comprises an absorbable carrier of a biocompatible, biodegradable polymer and dispersed, at least partially through or on said absorbable carrier, microparticles comprising fibrinogen in an amount of from about 0.1-15 mg/cm$^2$ or microparticles comprising thrombin in an amount of from about 0.01 to 500 IU/cm$^2$, wherein the microparticles further comprise a glassy carrier, wherein the absorbable carrier comprises chitosan, or derivative or salt or co-polymer thereof; gelatin, collagen or a polyurethane and wherein the absorbable carrier is preferably in the form of a porous matrix.

With reference to the term "partially through", it is intended that the microparticles are incorporated into the absorbable carrier at least at a single surface or more preferably present as a distribution presenting a concentration gradient relative to one of the surfaces of said absorbable carrier, or more preferably present as a homogenous distribution throughout said absorbable carrier. In a preferred configuration, the composition according to the invention does not include simple, non-agglomerated binary or tertiary blends of microparticles containing fibrinogen and/or microparticles containing thrombin and/or carrier microparticles, such as those described in WO 2010/136588.

In a seventeenth embodiment of the present invention, the pharmaceutical composition comprises an absorbable carrier of a biocompatible, biodegradable polymer and dispersed, at least partially through or on said absorbable carrier, microparticles comprising fibrinogen in an amount of from about 0.1-15 mg/cm$^2$ or about 0.5 to 5 mg/cm$^2$, or microparticles comprising thrombin in an amount of from about 0.01 to 500 IU/cm$^2$ and about 0.1 to 50 IU/cm$^2$, and wherein the microparticles further comprise a glassy carrier, wherein the absorbable carrier comprises chitosan, or derivative or salt or co-polymer thereof; gelatin, collagen or a polyurethane and wherein the absorbable carrier is preferably in the form of a porous matrix.

In an eighteenth embodiment of the present invention, the pharmaceutical composition comprises an absorbable carrier of a biocompatible, biodegradable polymer and dispersed and/or fixed, at least partially through or on said absorbable carrier, an homogenous mixture of microparticles comprising fibrinogen in an amount of from about 0.1-15 mg/cm$^2$ or about 0.5 to 5 mg/cm$^2$ and microparticles comprising thrombin in an amount of from about 0.01 to 500 IU/cm$^2$, or about 0.1 to 50 IU/cm$^2$, wherein the microparticles further comprise a glassy carrier, wherein the absorbable carrier comprises chitosan, or derivative or salt or co-polymer thereof; gelatin, collagen or a polyurethane and wherein the absorbable carrier is preferably in the form of a porous matrix.

In an nineteenth embodiment of the present invention, the pharmaceutical composition comprises an absorbable carrier of a biocompatible, biodegradable polymer and dispersed and/or fixed, at least partially through or on said absorbable carrier, an homogenous mixture of microparticles comprising fibrinogen in an amount of from about 0.1-15 mg/cm$^2$ or about 0.5 to 5 mg/cm$^2$ and microparticles comprising thrombin in an amount of from about 0.01 to 500 IU/cm$^2$, or about 0.1 to 50 IU/cm$^2$, wherein the microparticles further comprise a glassy carrier, wherein the absorbable carrier preferably comprises chitosan, or derivative or salt or co-polymer thereof; gelatin, collagen or a polyurethane, and wherein the absorbable carrier is preferably in the form of a porous matrix, whereby the composition, has a porosity or void fraction of between 1 and 99.9%, or about between 5 and 99%, or about between 10 and 98%, or about between 15 and 95%, wherein the porosity or void fraction is the fraction of the volume of voids over the total volume, expressed as a percentage. Alternatively, pores when present in the composition may have a diameter of from about 0.5 microns to about 5 mm, or from about 1 micron to about 1 mm or even from about 10 microns to about 500 microns.

In a further embodiment of the present invention, the pharmaceutical composition comprises an absorbable carrier of a biocompatible, biodegradable polymer and dispersed and/or fixed, at least partially through or on said absorbable carrier, an homogenous mixture of microparticles comprising fibrinogen and microparticles comprising thrombin in an amount of from about 5 mg/cm$^2$ to about 100 mg/cm$^2$, or from about 10 mg/cm$^2$ to about 90 mg/cm$^2$, or from about 20 mg/cm$^2$ to about 50 mg/cm$^2$, relative to the mass of total combined microparticles forming the mixture, wherein either and/or both the microparticles further comprise a glassy carrier, wherein the absorbable carrier preferably comprises chitosan, or derivative or salt or co-polymer thereof; gelatin, collagen or a polyurethane.

In a further embodiment of the present invention, the pharmaceutical composition comprises an absorbable carrier of a biocompatible, biodegradable polymer and dispersed, at least partially through or on said absorbable carrier, microparticles comprising fibrinogen in an amount of from about 0.1-15 mg/cm$^2$ or microparticles comprising thrombin in an amount of from about 0.01 to 500 IU/cm$^2$, wherein the microparticles further comprise a glassy carrier, wherein the absorbable carrier comprises chitosan, or derivative or salt or co-polymer thereof; gelatin, collagen or a polyurethane and wherein the absorbable carrier is preferably in the form of a porous and flexible matrix, which has at least one of the following physical properties: an elasticity module in the range of from about 5 to about 100 N/cm, such as from about 10 to 50 N/cm; and a density of from about 0.1 to 50 mg/cm$^3$, such as from about 1 to 10 mg/cm$^3$.

In another embodiment of the present invention is provided a composition for hemostasis, tissue sealing and tissue gluing which comprises an absorbable carrier of a biocompatible, biodegradable polymer and dispersed, at least partially through or on said absorbable carrier, microparticles comprising fibrinogen in an amount of from about 0.1-15 mg/cm$^2$ or microparticles comprising thrombin in an amount of from about 0.01 to 500 IU/cm$^2$, wherein the microparticles further comprise a glassy carrier, wherein the absorbable carrier comprises chitosan, or derivative or salt or co-polymer thereof; gelatin, collagen or a polyurethane and wherein the absorbable carrier is preferably in the form of a porous and/or flexible matrix, wherein the absorbable carrier has at least one of the following physical properties: an elasticity module in the range of from about 5 to about 100 N/cm, such as from about 10 to 50 N/cm; and a density of from about 0.1 to 50 mg/cm$^3$, such as from about 1 to 10 mg/cm$^3$.

In a further preferred embodiment of the present invention, the pharmaceutical composition comprises an absorbable carrier of a biocompatible, biodegradable polymer and dispersed, at least partially through or on said absorbable carrier, a mixture of microparticles comprising fibrinogen in an amount of from about 0.1-15 mg/cm$^2$ or about 0.5 to 5 mg/cm$^2$ and microparticles comprising thrombin in an amount of from about 0.01 to 500 IU/cm$^2$, or about 0.1 to 50 IU/cm$^2$, and wherein the microparticles further comprise a glassy carrier, wherein the absorbable carrier comprises chitosan, or derivative or salt or co-polymer thereof; gelatin, collagen or a polyurethane and wherein the absorbable carrier is preferably in the form of a porous matrix, and wherein the composition is in the form of a single, discrete, solid unit having a three-dimensional structure.

In a further embodiment of the present invention, the pharmaceutical composition comprises an absorbable carrier of a biocompatible, biodegradable polymer and dispersed, at least partially through or on said absorbable carrier, microparticles comprising fibrinogen in an amount of from about 0.1-15 mg/cm$^2$ or microparticles comprising thrombin in an amount of from about 0.01 to 500 IU/cm$^2$, wherein the microparticles further comprise a glassy carrier, wherein the composition is provided as a dry adhesive coating, aerosol, dry aerosol, pump spray, medical compress; film; coated plaster; medicated sponge or surgical patch, hemostatic fleece; hemostatic pad; gauze; salve, semi-gel, gel, foam, paste, suspension, ointment, emulsion, moldable form, nasal plug, surgical dressing, wound packing, bandage, swab, catheter, fibre optic, syringe, pessary, suppository, or suspension in a liquid or non-aqueous liquid.

In a further embodiment of the present invention, the pharmaceutical composition comprises an absorbable carrier of a biocompatible, biodegradable polymer and dispersed, at least partially through or on said absorbable carrier, microparticles comprising fibrinogen in an amount of from about 0.1-15 mg/cm$^2$ or microparticles comprising thrombin in an amount of from about 0.01 to 500 IU/cm$^2$, wherein the microparticles further comprise a glassy carrier, wherein the composition is provided as a single, discrete, solid unit having a three-dimensional structure, selected from a medical compress; film; coated plaster; medicated sponge, surgical patch, hemostatic fleece; hemostatic pad; gauze; moldable form, nasal plug, surgical dressing, wound packing, bandage, swab, catheter, fibre optic, syringe, pessary, or suppository.

The fibrinogen employed in a composition of the invention may be any suitable fibrinogen known and available to those skilled in the art. A specific fibrinogen for a particular application may be selected empirically by one skilled in the art. Preferably, the fibrinogen is a purified fibrinogen suitable for introduction to a patient.

The thrombin employed in a composition of the invention may be any suitable thrombin known and available to those skilled in the art. A specific thrombin source for a particular application may be selected empirically by one skilled in the art. Preferably, the thrombin is a purified thrombin suitable for introduction to a patient. The fibrinogen and the thrombin may be isolated from blood from human or animal donors (such as bovine thrombin), wherein the fibrinogen and/or the thrombin has been subjected to multiple purification steps, such as precipitation, concentration, diafiltration and affinity chromatography (preferably immunoaffinity chromatography), to remove substances which cause fragmentation, activation and/or degradation of the fibrinogen and/or thrombin during manufacture, storage and/or use of the pharmaceutical composition. In further embodiments, either or both the fibrinogen and/or thrombin may be made by recombinant DNA technology in cultured cells or via transgenic animals or plants.

The fibrinogen or thrombin may be full-length, wild-type (for fibrinogen containing an A alpha chain of 625 or 611 or 610 amino acids) or any active fragment thereof. Fragments are known; see Coller et al, J. Clin. Invest. 89:546-555 (1992). Also variants forms may be used. Suitable variant forms of fibrinogen include variants which are the result of alternative splicing, such as the so-called gamma prime (γ' variant) and the α-ext Fib or Fib420 variant, as disclosed in WO2010/004004 and herein incorporated by reference. Fibrinogen raw material may be a frozen solution, although, lyophilised powder which requires reconstitution prior to spray-drying may be used.

The content of fibrinogen in the microparticles comprising a glassy carrier may be from about 0.05 to 99.9% w/w, or from about 0.1 to 80% w/w, or about 0.5 to 60% w/w, as well as about 5 to 50% w/w, or about 10 to 25% w/w, or about 6.5% w/w. The content of thrombin in the microparticle comprising a glassy carrier may be from about 10 to 20,000 IU/g, or about 25 to 1000 IU/g, or about 100 to 500 IU/g, or about 270 IU/g.

The fibrinogen and/or thrombin-containing microparticles and/or additive material when present, may be solid or hollow, such as in the case of microcapsules. Microparticles comprising fibrinogen or thrombin may be prepared by methods known in the art, for example as described in WO 92/18164, WO 96/09814, WO 96/18388 or WO 97/44015, each of which is herein incorporated by reference. These spray-drying and associated particle manipulation processes enable the production of soluble protein microcapsules with defined size distribution, for example of up to 50 micrometers in diameter. For example, as described in those documents, the microparticles may be produced reproducibly, e.g. with 90% or more (by volume) up to 30 μm, e.g. 10 to 20 μm, in size. Readily-flowing agglomerates of these particles may be made in situ_by adjusting the air flow configuration in the spray-dryer to counter-current, or arranging multiple atomisers into a "forced primary agglomeration" set-up, as would be appreciated by persons skilled in the art. Such agglomerates may be 50 to 1000 microns or 100 to 500 microns, or 125 to 250 microns in diameter. Respective fibrinogen-containing and thrombin-containing soluble microparticles can be formulated and blended together within a spray-drying apparatus by the use of a multi-nozzle atomizer, as described in WO03/037303.

Although the preferred method of preparation of the microparticle components includes spray drying, other drying techniques may also be used to prepare said microparticles. Suitable methods are known in the art and include fluidized bed drying and freeze-drying, with subsequent micronisation, or via spray-freeze drying. Microparticles may be sterilised, if necessary or desired, using techniques known in the art.

Microparticles used in forming compositions according to the invention are preferably prepared by spray-drying. Typically, a 2-fluid nozzle is used which utilises compressed air during the atomisation process; this results in the production of hollow microparticles. The maximum particle size of microparticles (volume median diameter; X50, as measured by Sympatec) that can be manufactured using this atomisation system on the Niro Mobile Minor spray dryer is ~30 μm. Preferred X50 values for the microparticles of the invention are between about 1 and 50 microns, most preferably between about 10 and 30 microns, or about between 15 and 25 microns.

The solid or hollow fibrinogen-containing microparticles are then blended first, with the solid or hollow thrombin-containing microparticles and optionally then with the additive material as described herein, vice versa, or in any sequence which produces a homogenous blend. Such blending can be carried out using low shear or high-shear blending, or any other technique known to persons skilled in the art.

Microparticles of the invention may be prepared by spray-drying a solution of the active component with a saccharide alone, such as mono- and di-saccharides, including lactose, mannitol and trehalose, or polysaccharides such as dextran. An alternative procedure comprises co-spray-drying, in which fibrinogen or thrombin and another wall-forming material are formulated and spray-dried, to give microparticles in which the active component is incorporated into the particle. Suitable other proteins may be naturally occurring or be made by recombinant DNA technology in cultured cells or transgenic animals or plants. They may act as "wall-forming materials", as described in WO92/18164, where various examples are given. A preferred material is HSA (human serum albumin). For example, fibrinogen is spray-dried alone or in the presence of varying amounts of excipients such as HSA (e.g. fibrinogen: HSA ratios of 1:1, 1:3, 3:1) and trehalose. Other suitable substitutes for HSA include surfactants, such as Tween 20, Tween 80, Poloxamer 407 or Poloxamer 188. Calcium ion, e.g. as calcium chloride, may be incorporated in the thrombin feedstock. Alternatively, calcium chloride may be added to the microparticles after processing.

In a further embodiment of the invention, an additive material may also be present. The additive material used in the invention typically has a particle size of 10 nm to 1 mm or about 10 microns to 1000 μm. Where the additive is chosen to act as a carrier, the particle size may be between 10 to 1000 μm, or 100 to 500 μm, or 125 to 250 μm or possibly e.g. 10 to 40 μm. They may comprise one material or a mixture.

The additive material may comprise about 1%, about 2%, about 3%, about 4% about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, by weight of the microparticle blend of the composition, or any range between.

Various materials are suitable for use as a biocompatible, water-absorbent, water-swellable additive material, for enhancing flow and wettability, etc. Preferably the material is insoluble or very slowly soluble. Such materials may include dextran polymers, like e.g. Sephadex, which are available in different particle sizes, starches, pullulan derivatives, hyaluronic acid esters, cellulose products such as microcrystalline cellulose (Avicel range), methylcellulose, carboxymethyl cellulose, microfine cellulose or hydroxy propyl cellulose, hydroxypropylmethylcellulose, hydroxypropylcellulose, low-substituted hydroxypropyl cellulose, hydroxyethylcellulose and other materials such as cross-linked polyvinyl pyrrolidone (PVP), may be used singly or in admixture. Also, suitable additive materials acting as carriers include polyethylene glycol (PEG), preferably having a molecular weight of about 1000; polyvinylpyrrolidone (PVP), preferably having an average molecular weight of about 50,000; Poly(acrylic acid), polyacrylamide, poly vinyl alcohol (PVA), Poly(methylvinylether co-maleic anhydride), Poly(ethyleneoxide), and dextran, typically having an average molecular weight of about 40,000. Microparticles incorporated into pharmaceutical compositions of the invention, or the compositions themselves, may be sterilised, if necessary or desired. Sterile processing, electron beam irradiation, γ-irradiation and ethylene oxide are examples of suitable techniques.

The additional particles used in the invention (described herein as "carrier particles") typically have a particle size of 10 to 1000 μm, e.g. 10 to 40 μm. They may comprise one material or a mixture. Various materials are suitable for the large carrier materials for fibrin sealant, for enhancing flow and wettability, etc. They include saccharides such as mono- and di-saccharides, including lactose, mannitol and trehalose, or dextran and dextran polymers, like e.g. Sephadex, which are available in different particle sizes.

Cellulose products such as microcrystalline cellulose (Avicel range), methylcellulose, carboxymethyl cellulose, microfine cellulose or hydroxy propyl cellulose, and other materials such as cross-linked polyvinyl pyrrolidone (PVP), may be used singly or in admixture as the carrier particles. Also, suitable carrier particles may comprise polyethylene glycol (PEG), preferably having a molecular weight of about 1000; polyvinylpyrrolidone (PVP), preferably having an average molecular weight of about 50,000; Poly(acrylic acid), PVA, Poly(methylvinylether co-maleic anhydride), Poly(ethyleneoxide), and dextran, typically having an average molecular weight of about 40,000.

Tablet disintegrants are examples of additive materials which may be included within the microparticle blend incorporated into a composition according to the invention. These materials will absorb moisture from the wound, expand rapidly and thereby enhance the wettability of the hemostatic components of the powder blend:

Sodium starch glycolate (Explotab® or Primojel®)—has an average particle size in the range of 35-55 μm. About 25% of the glucose units are carboxymethylated.

cross-linked polyvinyl pyrrolidone (Polyplasdone®)
alginates and alginic acid
cross-linked sodium carboxymethylcellulose (Ac-Di-Sol®)

Gums and gelling agents that can be used include, for example, Tragacanth, Karaya gum, soluble starch, Gelatin, Pectin, Guar gum and Gellan gum. A particularly preferred additive is Emdex®, i.e. a hydrated form of dextrates (spray crystallized dextrose containing small amounts of starch oligosaccharides). It is a highly refined product composed of white, free-flowing, spray-crystallized macroporous spheres with a median particle size of 190-220 μm. Another preferred additive is NON-PAREIL SEEDS®: (Sugar Spheres). These are used in multiple drug units for improved content uniformity, consistent and controlled drug release and high drug stability, size ranges from 200 to 2000 mm. Another suitable carrier additive is sorbitol or mannitol in the highly porous and highly soluble interwoven filamentary crystal form as sold under the name PARTECK SI® and PARTECK M® (Merck KGaA, Darmstadt, Germany). These grades have a high adsorption capacity and so are suitable for blending with the dry powder fibrin sealant powder present in compositions of the invention, to produce a novel powder for incorporation which reduces dusting, enhances wettability, solubilisation and performance of the dry powder fibrin sealant and/or compositions of the invention, by allowing blood to soak through the composition and thus avoid clotting at the interface alone.

In another embodiment of the invention, the microparticles or blend thereof, incorporated into a composition according to the invention, may further comprise an effervescent couple. The gas produced following an effervescent reaction can expand the fibrin sealant into a 'foam' and/or increase wettability of the powders comprising the fibrin sealant. As the powders are applied to a wound, the effervescent components dissolve, react and liberate, say, carbon dioxide, thereby increasing the wettability of the hemostatic components and thus enhancing time to clot formation. The fibrin sealant will appear as a stable foam once fully reacted and the clot has formed. The effervescent couple typically comprises citric acid or sodium hydrogen citrate and sodium bicarbonate, but other physiologically acceptable acid/alkaline or alkaline earth metal carbonate mixtures may be used, for example tartaric, adipic, fumaric or malic acids, and sodium, potassium or calcium (bi)carbonates or sodium glycine carbonate. In general it has been found that preferred taste characteristics are exhibited when the relative proportions of the components of the effervescent couple on a chemical molecular equivalent basis are in the range of 4:3 to 1:3, more preferably about 2:3, expressed as the ratio of molecular equivalent of the acidic component to the basic component. In terms of a preferred combination of citric acid and sodium bicarbonate these values represent on a weight basis, a range from 1:1 to 0.3:1, preferably 0.5:1 expressed as the ratio of acidic to basic component.

Another preferred additive material is a silica, preferably those that are hydrophilic. Such silicas may be colloidal silicas, fumed silicas, ground silicas, precipitated silicas, or mixtures thereof. Examples of suitable fumed silicas include but are not limited to, Aerosil® 90, 130, 150, 200, 300, 380, R202, R805, R812, R972, R974 (Degussa Corporation, Ridgefield Park, N.J.) and CAB-O-SIL® TS-720 and M-5 (Cabot Corporation, Tuscola, Ill.). Generally, Aerosil.®. 200, Aerosil® . . . R974, CAB-O-SIL.®. TS-720 and any other generally equivalent products from other manufacturers of fumed silicas are preferred. It is known that hydrophilic AEROSIL® colloidal silica increases the rate of tablet disintegration and active ingredient release. The colloidal silica acts as a "wick" to draw the water—for example from the digestive juices—into the interior of the tablet. Moreover, tablet ingredients "coated" with hydrophilic AEROSIL® 200 colloidal silica are more easily wetted and swell faster (disintegrants) or dissolve faster (active ingredient). Such properties enhance the wettability and dissolution of the dry powder fibrin sealant and/or microparticles incorporated into compositions of the instant invention. Furthermore, such silicas are known to act as glidants, and so will enhance the flowability, filling and delivery of such cohesive microparticulates during manufacture of the compositions of the invention. Moreover, such colloidal silicas are known activators for blood clotting and thus act synergistically with the fibrinogen and thrombin components (see Margolis, "The Effect of Colloidal Silica on Blood Coagulation", Aust. J. Exp. Biol., 39, pp. 249-258 (1961)). The composition of the invention may comprise between 0.0001 to 5% w/w, or about 0.001 to 2% or about 0.01 to 0.5% w/w of a silica. The silica may be simply blended with the fibrinogen-containing component and then the thrombin-containing component added thereto and blended further, or vice versa. Most preferably the silica is blended with the pre-blended powdered components as a final step, before incorporation with the absorbable carrier, as described herein. Suitable blending apparatus will be known to those skilled in the art, the silica may be present in combination with a carrier additive particle, as defined herein.

The additive material may be present in the microparticle blend incorporated into a composition according to the invention, as single components or in combination and may be present in the feedstock or added to either the spray-dried thrombin or fibrinogen component before blending together, or added to the final blend and subjected to further blending. Such blending can be carried out using low shear or high-shear blending, mechano-chemical bonding, hybridisation or any other technique known to persons skilled in the art.

Although the components of the microparticles are preferably water-soluble, and the microparticles are preferably obtained by spray-drying a suitable solution, the microparticles that are obtainable may be free-flowing, discrete and substantially dry or anhydrous, with a residual moisture content preferably not greater than about 8% w/w, most preferably not greater than about 5 or about 3% w/w. This means that the microparticle components used in accordance with this invention are not activated until they are wetted, e.g. by coming into contact with liquid at a wound site. The active-containing fibrinogen and/or thrombin microparticles are preferably amorphous or in the form of a glass at room temperature (e.g. 25 degrees Celsius), or comprise a glassy carrier, so as to stabilise the entrapped protein as well as present the active in such a rapidly-soluble state. Preferably either or both of the fibrinogen and/or thrombin-containing microparticles exhibit a glass transition temperature of greater than about 25 degrees Celsius, or about 30 degrees Celsius, or about 40 degrees Celsius, or about 50 degrees Celsius, or more suitably about 60 degrees Celsius, or about 70 degrees Celsius, or about 80 degrees Celsius, or greater, as measured by Differential Scanning calorimetry or modulated Differential Scanning calorimetry. The carrier, diluent or excipient, or combinations thereof, present in either or both of the fibrinogen and/or thrombin-containing microparticles exhibit a glass transition temperature of greater than about 25 degrees Celsius, or about 30 degrees Celsius, or about 40 degrees Celsius, or about 50 degrees Celsius, or more suitably about 60 degrees Celsius, or about 70 degrees Celsius, or about 80 degrees Celsius, or greater, as measured by Differential Scanning calorimetry or modulated Differential Scanning Calorimetry. In such a physical state, the carrier, diluent or excipient is therefore glassy. Preferably, the glassy carrier has a degree of crystallinity, as measured by FTIR, of at most about 10% by weight of the microparticle population in the composition, more preferably at most about 8% and even more preferably at most about 6%.

In another embodiment of the invention, the glassy carrier comprises a glass former selected from the group consisting of carbohydrates, carbohydrate derivatives, carbohydrate polymers, organic carboxylic acid salts, synthetic organic polymers, proteins, peptides, amino acids, and mixtures thereof. Preferably, the glassy carrier comprises a glass former selected from the group consisting of carbohydrates, peptides, and amino acids. Most preferably, the glassy carrier comprises a glass former selected from the group consisting of sodium citrate, raffinose, lactose, trehalose, maltotriose, maltodextrin, maltose, glucopyranosyl-sorbitol, glucopyranosyl-mannitol, polydextrose, sucrose, cyclodextrin, casein, human serum albumin, hydroxyethyl starch, stachyose, magnesium gluconate, cellobiose, and mixtures thereof. In a most preferred embodiment, the glassy carrier comprises trehalose.

In another embodiment, microparticles consisting essentially of amorphous fibrinogen and/or amorphous thrombin are employed. The amorphous fibrinogen and/or amorphous thrombin exhibit a glass transition temperature of greater than about 25 degrees Celsius, or about 30 degrees Celsius, or about 40 degrees Celsius, or about 50 degrees Celsius, or more suitably about 60 degrees Celsius, or about 70 degrees Celsius, or about 80 degrees Celsius, or greater, as measured by Differential Scanning calorimetry or modulated Differential Scanning calorimetry. In such a physical state, the carrier, diluent or excipient is therefore glassy. Preferably, the amorphous fibrinogen and/or amorphous thrombin microparticles exhibit a degree of crystallinity, as measured by FTIR, of at most about 10% by weight of the microparticle population in the composition, more preferably at most about 8% and even more preferably at most about 6%.

A preferred process for production of said amorphous fibrinogen or thrombin particles is via spray-drying, as described in U.S. Pat. No. 6,926,908. Incorporation of said spray-dried microparticles into or on the absorbable carrier is preferably with the aid of cooled anhydrous solvents, such as ethanol at −30° C.

The additive material may also be amorphous or in the form of a glass at room temperature (e.g. 25 degrees Celsius) so as to be in a rapidly-soluble state. Preferably the fibrinogen and/or thrombin containing microparticles of the composition exhibits a glass transition temperature of greater than about 25 degrees C., or about 30 degrees C., or about 40 degrees C., or about 50 degrees C., or more suitably about 60 degrees Celsius, or about 70 degrees Celsius, or about 80 degrees Celsius, or greater, as measured by Differential Scanning calorimetry or modulated Differential Scanning calorimetry. Such glassy compositions enable the composition to be stored at ambient or room temperature, e.g. 25 degrees C., for extended periods of time, for example greater than 3 months or greater than 6 months, without significant losses in activity. Significant losses are defined as losses in activity of greater than about 5 or 10 or 20 percent or more of original potency of either or both of fibrinogen and/or thrombin.

The additive material may also be in a crystalline or amorphous state but also be free-flowing, discrete and substantially anhydrous, with a residual moisture content preferably not greater than about 5% w/w, most preferably not greater than about 3% w/w.

In yet another embodiment of the invention, the composition is adapted to form a protective or preventative covering or bandage for minor abrasions, cuts, scrapes, scratches, burns, sunburns, ulcers and other skin injuries and irritations, such as bleeding during and post-surgery, and uncontrolled internal and external haemorrhage from heavy trauma and/or battlefield wounds.

In another embodiment of the invention, the pharmaceutical composition can be used as a topical hemostat to stop bleeding. In the present context, the time it takes to stop bleeding is called the time to hemostasis (TTH). If a pressure sheet is used, measurement of TTH typically starts when a pressure sheet is applied to the bleeding site, pressure subsequently being applied, and runs until bleeding has stopped, by visualization of the dressing and/or an indication of bleeding through or around the dressing, is not observed.

In a further embodiment of the invention is provided a method of treating a wound or the use of a composition according to the invention as a hemostat wherein application of the pharmaceutical composition to a wound results in a TTH of about 10 minutes or less, about 5 minutes or less, or about 3 minutes or less.

In a further embodiment of the invention is provided a method of treating a wound or reducing bleeding at a haemorrhaging site, or the use of a composition according to the invention as a hemostat wherein application of the pharmaceutical composition to a wound results in a post-treatment blood loss of less than about 100 ml/kg, or less than about 80 ml/kg, or less than about 60 ml/kg, or less than about 40 ml/kg, optionally wherein the pre-treatment blood loss is at least about 5 ml/kg, or at least about 10 ml/kg, or at least about 15 ml/kg, or at least about 50 ml/kg, or at least about 100 ml/kg or more.

In a further embodiment of the invention is provided a method of treating a wound or reducing bleeding at a haemorrhaging site, or the use of a composition according to the invention as a hemostat wherein application of the pharmaceutical composition to a wound results in a reduction in Mean Arterial Pressure (MAP) 60 minutes post injury and relative to pre-injury, of less than about 40 mmHg, or less than about 30 mmHg, or less than about 20 mmHg, or less than about 10 mmHg or less than about 5 mmHg or less than about 3 mmHg, or even no change in MAP relative to pre-injury MAP. Accordingly, it is desired that the MAP is maintained as close to the pre-injury MAP as possible, for as long as possible, in order to enhance the subject's chance of survival and reduce the need for infusions and/or transfusions.

In a further embodiment of the invention is provided a method of treating a wound or reducing bleeding at a haemorrhaging site, or the use of a composition according to the invention as a hemostat wherein application of the pharmaceutical composition to a wound results in a survival time of at least about 60 minutes, or at least about 90 minutes, or at least about 120 minutes, or at least about 180 minutes, or more.

In a further embodiment of the invention is provided a method of treating a wound or reducing bleeding at a haemorrhaging site, or the use of a composition according to the invention as a hemostat wherein application of the pharmaceutical composition to a wound results in a percent survival of at least about 10 percent, or at least about 20 percent, or at least about 30 percent, or at least about 40 percent, or at least about 50 percent, or at least about 75 percent, or at least about 90 percent, or at least about 95 percent, or more.

In a further embodiment of the invention is provided a method of treating a wound or reducing bleeding at a haemorrhaging site, or the use of a composition according to the invention for hemostasis, tissue sealing and tissue gluing, wherein application or use of the pharmaceutical composition further comprises the application of moderate manual pressure for not less than about 30 seconds, or not less than about 60 seconds, or not less than about 2 minutes, or not less than about 3 minutes, or not less than about 5 minutes, or not less than about 7 minutes, or not less than about 10 minutes, or longer.

In a further embodiment of the invention is provided a method of treating a wound or reducing bleeding at a haemorrhaging site, or the use of a composition according to the invention for hemostasis, tissue sealing and tissue gluing, wherein application or use of the pharmaceutical composition further comprises the application of moderate manual pressure for not less than about 30 seconds, or not less than about 60 seconds, or not less than about 2 minutes, or not less than about 3 minutes, or not less than about 5 minutes, or not less than about 7 minutes, or not less than about 10 minutes, or longer, and wherein said treatment results in a time to hemostasis (TTH) of less than about 10 minutes, or less than about 8 minutes, or less than about 5 minutes, or less than about 4 minutes, or less than about 3 minutes, or less than about 2 minutes, when administered to a wound which exhibits a bleeding rate of greater than about 30 gram/minute, or more.

Another embodiment of the invention is the use of the pharmaceutical compositions as described herein for the treatment of mild to moderate bleeding. Mild bleeds are those typically presenting with a blood flow of less than about 5 g/minute whereas moderate bleeds are often about 10 g/minute or less, or about 20 g/minute, or less, optionally with a TTH of less than 10 minutes, or about 5 minutes or less.

In a preferred embodiment of the invention is provided the use of the pharmaceutical compositions as described herein for the treatment severe bleeding. Severe bleeds are those typically presenting with a blood flow or loss of more than about 30 g/minute, or more than about 40 g/minute, or more than about 50 g/minute, or more than about 60 g/minute, or more than about 100 g/minute, or even more than about 150 g/minute or greater. Accordingly, there is provided composition for treatment of severe or uncontrolled bleeding in a subject in need thereof, wherein the blood flow or loss in said subject is more than about 30 g/minute, or more than about 40 g/minute, or more than about 50 g/minute, or more than about 60 g/minute, or more than about 100 g/minute, or even more than about 150 g/minute or greater, and optionally wherein said treatment results in a TTH of less than about 10 minutes, or less than about 5 minutes or less. In situations where there is such a great rate of bleeding, it is common for there to be a concomitant need for transfusions of blood products and/or infusion of volume expanders, etc.

In another embodiment of the invention, is provided a composition for treatment of severe or uncontrolled bleeding and/or reducing bleeding at a haemorrhaging site in a subject in need thereof, wherein the blood flow or loss in said subject is more than about 30 g/minute, or more than about 40 g/minute, or more than about 50 g/minute, or more than about 60 g/minute, or more than about 100 g/minute, or even more than about 150 g/minute or greater, and optionally wherein said treatment results in a TTH of less than about 10 minutes, or less than about 5 minutes or less, and wherein the duration of severe or uncontrolled bleeding prior to treatment is at least about 2 minutes, or at least about 5 minutes, or at least about 10 minutes, or more.

In another embodiment of the invention, is provided a method of treatment of severe or uncontrolled bleeding and/or reducing bleeding at a haemorrhaging site in a subject in need thereof, wherein the blood flow or loss in said subject is more than about 30 g/minute, or more than about 40 g/minute, or more than about 50 g/minute, or more than about 60 g/minute, or more than about 100 g/minute, or even more than about 150 g/minute or greater, and optionally wherein said treatment results in a TTH of less than about 10 minutes, or less than about 5 minutes or less, and wherein the duration of severe or uncontrolled bleeding prior to treatment is at least about 2 minutes, or at least about 5 minutes, or at least about 10 minutes, or more.

Another object of the present invention is to provide a pharmaceutical composition adapted to form a seal on non-superficial tissues or to close open tissues exceeding minor abrasions, cuts, scrapes, scratches, burns, sunburns, ulcers and other skin injuries and irritations. Treatable wounds include: topical wounds; deeper wounds; surgical incisions; severe wounds; battlefield wounds and trauma; and emergency room excessive bleeding, among others. Accordingly, the various applications of the wound sealants include first aid and triage applications for surgical and medical procedures. A pharmaceutical composition of the invention may be applied directly to wounds, sutures, incisions and other openings where bleeding may occur. A wound includes damage to any tissue in a living organism. A biological tissue includes connective tissues, endothelial tissues, nervous tissues, muscle tissue and organs. Preferred biological tissues are selected from the group consisting of bone, skin, cartilage, spleen, muscle, lymphatic, renal, hepatic, blood vessels, lung, dura, bowel and digestive tissue. The tissue may be an internal (e.g. organ) or external tissue (e.g. eye, skin, etc.), and may be a hard tissue (e.g. bone) or a soft tissue (e.g. liver, spleen etc.). The wound may have been caused by any agent, including infection, surgical intervention, burn or trauma. Trauma is defined as an injury caused by a physical force; examples include the consequences of motor vehicle accidents, gunshots and burns.

In a further embodiment of the invention, the compositions of the invention are administered during or after surgery. The compositions of the invention may be administered to the wound or wounds of a subject, including human, mammal and other veterinary applications.

The invention further comprises a method of treating a wound or for reducing bleeding at a haemorrhaging site by applying or administering a composition as described herein.

In a further embodiment of the invention, the pharmaceutical composition is formulated and packaged as either as a non-sterile or sterile preparation for single-delivery application to a wound site, or as a multi-use preparation.

The pharmaceutical compositions of the invention are applied topically to a wound site. Alternatively or in addition, the composition can be introduced internally into the wound site in the case of, for example, deeper lacerations, arterial wounds, or during surgical procedures.

In a further embodiment of the invention is provided a liquid composition comprising a suspension of a mixture of first microparticles that comprise fibrinogen and/or second microparticles that comprise thrombin in a non-aqueous vehicle, optionally wherein either or both first and second microparticles further comprise a glassy carrier, and optionally wherein the liquid composition further comprises an additive or as described herein, for topical delivery on minor abrasions, cuts, scrapes, scratches, burns, sunburns, ulcers, internal venous bleeding, external venous bleeding, limited access wounds, space-filling applications and surgical trauma. The composition may be easily applied to the wound site in variable quantities and will quickly stop bleeding.

The invention also comprises a process for preparing a water-soluble fibrin sealant paste, salve, ointment or suspension composition comprising the steps of: admixing the microparticle components of a composition of the invention and/or blend thereof, and a liquid, biocompatible, biodegradable polymer vehicle, such as a polyethylene glycol having a molecular weight range of from about 200 to 6000. Preferably blends of various molecular weights of PEG are used. Preferably, the PEG is a blend having an average molecular weight of in the range of 500 to 1,000, as a 1:1, or 1:2 or 1:3 or 1:5 or 1:9 blend of PEG 300 MW and 1500 MW. Use of lower grades of PEG will produce lighter, less viscous suspensions which can be packaged and delivered via a pump spray. Such suspensions may optionally include a surfactant or other suitable suspending agent, to prevent flocculation. Preparation and the formulation of such formats are known to those skilled in the art. The paste, salve, ointment or suspension composition may also be used in conjunction with, for example, a gelatin sponge, gauze or collagen material by either coating such material as a substrate with the composition and applying it to the haemorrhaging site or first applying the composition to a haemorrhaging site and placing the gelatin sponge, gauze or collagen on top of the composition and applying pressure thereto. The ointment, salve or paste of the present invention has a viscosity and potency which is high enough to permit its hemostatic effective use by a surgeon by dipping of a gloved finger into the paste and placing the paste over the bleeding site. The polyethylene glycol that is used in this aspect has an average molecular weight range of from about 500 to 1000 or more preferably about 900. Grades of polyethylene glycol can be combined with one another to produce unique properties. For example, PEG 1500, a solid at room temperature, while not soluble in liquid PEG 300 at room temperature may be combined together and heated above the melting point of the higher melting glycol (i.e. PEG 1500) to form a solution. For example, PEG 300 which is a liquid, is mixed with an equal weight of PEG 1500, a solid melting at 43 degrees C., and the two heated together at or above the melting point of PEG 1500 such that they liquify to a homogeneous solution, and when that solution is cooled to room temperature, it forms a smooth, soft paste. This paste is water soluble, and sufficiently yielding to spread readily on tissue or skin. Other suitable non-aqueous vehicles will be known to the skilled artisan.

The invention further comprises a method of treating a wound or for reducing bleeding at a haemorrhaging site by applying a paste composition comprising a hemostatic effective amount of a mixture of first microparticles that comprise fibrinogen and second microparticles that comprise thrombin, optionally wherein either or both first and second microparticles further comprise a glassy carrier, in a base comprising a liquid, biocompatible, biodegradable polymer vehicle, such as a polyethylene glycol, to the haemorrhaging site of a patient. The paste may be applied in combination with a fibrous gauze material or by itself in paste form to the haemorrhaging site.

In a further embodiment of the invention, the microparticle components of a composition according to the invention, and/or blend thereof, is admixed with a propellant and packaged in an aerosol container, optionally with a polymer such as PVP (see U.S. Pat. No. 4,752,466). This therefore provides a convenient way to deliver dry powdered thrombin directly to a wound, or directly onto a hemostat or support material as described herein. The amount of fibrin sealant powder composition used in each can could differ according to the potency desired, but typically might be in the order of magnitude of about 0.5 to about 1.0 gram or more. The propellant, in liquified form, is then filled into the aerosol container through the valve from a tank where it exists in liquified form. The amount of propellant used typically might be in the order of about 10 grams. Other methods of filling an aerosol container are well known and may be used if desired. Inside the aerosol container, the biocompatible, biodegradable polymer e.g. PVP, may be completely dissolved in the propellant. The fibrin sealant powder composition does not dissolve, but exists in a very finely divided state, i.e., it is suspended in the propellant, where it exists as a finely divided milky suspension. When the valve is depressed to spray the material from the aerosol container, a mixture of fibrin sealant powder composition, propellant and biocompatible, biodegradable polymer, is emitted. The propellant evaporates quickly and disappears. Aerosol containers and components thereof designed for dispensing powder sprays are commercially available, and may be used in the present invention. In the "Handbook of Aerosol Technology" by Paul Sanders (Van Nostrand, Reinhold Company, N.Y. 1979, 2nd. ed. Chapter 21 entitled "Aerosol Suspensions) (Powders) gives background information. Preferred propellants include those of the HFA series.

The aerosol package of the present invention should be prepared and handled in such manner that its contents will be sterile when sprayed. The use of bacterial filters and aseptic processing techniques results in a sterile product. The aerosol of the present invention is designed to be stored at room temperature. In this form it is relatively stable for at least for periods of 6 months due to the glassy nature of the microparticle components of the composition.

In a most preferred embodiment of the invention is provided a pharmaceutical composition comprising an absorbable carrier of a biocompatible, biodegradable polymer, and dispersed at least partially through, in or on said absorbable carrier, a mixture of first microparticles that comprise fibrinogen and/or second microparticles that comprise thrombin, optionally wherein either or both first and/or second microparticles further comprise a glassy carrier, for use in surgical interventions such as such as in the gastrointestinal system, e.g. the oesophagus, stomach, small intestine, large intestine, bowel, rectum, on parenchymal organs such as the liver, pancreas, spleen, lungs, kidney, adrenal glands, lymph and thyroid glands; surgical interventions in the ear, nose and throat area (ENT) including dental surgery, epistaxis, cardiovascular surgery, such as carotid endarterectomy, femoropopliteal bypass or coronary artery bypass grafting (CABG); aesthetic surgery, spinal surgery, neurological surgery, such as posterior lumbar interbody fusion, microdiscectomy or craniotomy; lymphatic, biliary, and cerebrospinal (CSF) fistulae, air leakages during thoracic and pulmonary surgery, thoracic surgery including surgery of the trachea, bronchi and lungs; orthopaedic surgery, such as knee or hip replacement; gynaecological surgical procedures such as caesarian section, hysterectomy, fibroid surgery; vascular surgery, such as shunts; urological, bone (e.g. spongiosa resection), and emergency surgery. Particularly preferred surgical interventions include orthopaedic surgery, liver resection, soft tissue injury/surgery and vascular surgery. The composition may be applied with a layer of the mixture of microparticles, if present, adjacent to the wound surface, or where the layer is on the opposite side to that applied to the wound surface.

In a further preferred embodiment of the invention is provided a pharmaceutical composition comprising an absorbable carrier of a biocompatible, biodegradable polymer, and dispersed at least partially through, in or on said absorbable carrier, a mixture of first microparticles that comprise fibrinogen and/or second microparticles that comprise thrombin, optionally wherein either or both first and/or second microparticles further comprise a glassy carrier and wherein the composition is provided and/or packaged as a dry adhesive coating, aerosol, dry aerosol, pump spray, medical compress; film; coated plaster; medicated sponge or surgical patch, hemostatic fleece; hemostatic pad; gauze; salve, semi-gel, gel, foam, paste, suspension, ointment, emulsion, moldable form, nasal plug, surgical dressing, wound packing, bandage, swab, catheter, fibre optic, syringe, pessary, suppository, or suspension in a liquid or non-aqueous liquid.

In a most preferred embodiment of the invention is provided a pharmaceutical composition wherein the absorbable carrier comprises a biocompatible, biodegradable polymer selected from the group consisting of polysaccharides, albumin, a cellulose, methylcellulose, alkylhydroxyalkyl cellulose, hydroxyalkyl cellulose, cellulose sulfate, salts of carboxymethyl cellulose, carboxymethyl cellulose, carboxyethyl cellulose, oxidised cellulose; gelatins or collagen, such as a collagen-sponge, chitin, carboxymethyl chitin, hyaluronic acid, salts of hyaluronic acid, alginate, alginic acid, propylene glycol alginate, glycogen, dextran, dextran sulfate, curdlan, pectin, pullulan, xanthan, chondroitin, chondroitin sulfates, carboxymethyl dextran, carboxymethyl chitosan, chitosan, heparin, heparin sulfate, heparan, heparan sulfate, dermatan sulfate, keratan sulfate, carrageenans, starch, amylose, amylopectin, poly-N-glucosamine, poly-N-acetyl glucosamine, polymannuronic acid, polyglucuronic acid, polyguluronic acid, chitosan, carboxymethyl chitosan, chitosan salts; a polyurethane; oxidised polysaccharides, and derivatives or combinations of any of the above.

Other preferred biocompatible, biodegradable polymers for use in this embodiment of the invention, include polyurethanes and absorbable carriers formed from a polyurethane, such as those disclosed in WO 2004/062704 and WO 2010/137981 (Polyganics B.V), herein incorporated by reference.

Yet further preferred biocompatible, biodegradable polymers for use in this embodiment of the invention, include chitin, chitin-glucan, chitosan, chitosan-glucan, derivatives thereof, and any combinations thereof, and absorbable carriers formed from such polymers and combinations, such as those disclosed in WO 2010/142507 and WO 2007/122187 (Kitozyme S. A), herein incorporated by reference.

In another embodiment of the invention is provided a pharmaceutical composition comprising an absorbable carrier of a biocompatible, biodegradable polymer, and dispersed at least partially through, in or on said absorbable carrier, a mixture of first microparticles that comprise fibrinogen and/or second microparticles that comprise thrombin, optionally wherein either or both first and/or second microparticles further comprise a glassy carrier, wherein the absorbable carrier comprises a chitosan or derivative or co-polymer or salt thereof, optionally which is not of fungal origin.

In another preferred embodiment of the invention is provided a pharmaceutical composition comprising an absorbable carrier of a biocompatible, biodegradable polymer, and dispersed at least partially through, in or on said absorbable carrier, a mixture of first microparticles that comprise fibrinogen and/or second microparticles that comprise thrombin, optionally wherein either or both first and/or second microparticles further comprise a glassy carrier, wherein the absorbable carrier comprises a support material, such as a gauze, sponge, pad, bandage and the like.

It is proposed herein to spray, drip, dip, impregnate or otherwise embed or apply the microparticle components of a composition according to the invention, and/or blend thereof, in predetermined strengths such as for example: 20%, 40%, 60% or 80%, or any other preferred strengths, on the support and identify the strength of the fibrin sealant powder applied thereon. Methods of application of the microparticle components and/or blend thereof, or combinations of the microparticle components and other materials as described herein, into, onto or throughout the support material, are well known to those skilled in the art.

In another preferred embodiment of the invention is provided a pharmaceutical composition comprising an absorbable carrier of a biocompatible, biodegradable polymer, and dispersed at least partially through, in or on said absorbable carrier, a mixture of first microparticles that comprise fibrinogen and second microparticles that comprise thrombin, optionally wherein either or both first and second microparticles further comprise a glassy carrier, wherein the absorbable carrier comprises a support material, such as a gauze, sponge, pad, bandage and the like, and wherein the first and second microparticles are dispersed and/or fixed through, in or on said absorbable carrier.

In another preferred embodiment of the invention is provided a pharmaceutical composition comprising an absorbable carrier of a biocompatible, biodegradable polymer, and dispersed at least partially through, in or on said absorbable carrier, a mixture of first microparticles that comprise fibrinogen and/or second microparticles that comprise thrombin, optionally wherein either or both first and/or second microparticles further comprise a glassy carrier, wherein the absorbable carrier comprises a support material, such as a gauze, sponge, pad, bandage and the like, and wherein the first and/or second microparticles are dispersed and/or fixed substantially homogeneously through, in or on said absorbable carrier.

Suitable vehicles include, but are not limited to carriers, solvent, perfluorocarbons and the like. Most preferred vehicles are solvents classified under the ICH Guidelines as either class 2 or Class 3. Suitable such solvents in Class 2 include acetonitrile, cyclohexane, dichloromethane, 1,4-dioxane, ethylene glycol, hexane, methanol, toluene, xylene, and the like. Suitable such solvents in Class 3 include acetone, anisole, 1-butanol, 2-butanol, butyl acetate, heptane, isopropyl acetate, methylethyl ketone, 2-methyl-1-propanol, dimethylsulfoxide, ethanol, ethyl acetate, ethyl ether, ethyl formate, pentane, 1-pentanol, 2-propanol, and the like. In a most preferred method is the use of ethanol or 1,4-dioxane.

In another preferred embodiment of the invention is provided a method of making a pharmaceutical composition comprising an absorbable carrier of a biocompatible, biodegradable polymer, and dispersed at least partially through, in or on said absorbable carrier, a mixture of first microparticles that comprise fibrinogen and/or second microparticles that comprise thrombin, optionally wherein either or both first and/or second microparticles further comprise a glassy carrier, wherein the absorbable carrier comprises a support material, such as a gauze, sponge, pad, bandage and the like, and the method includes the steps of; (i), forming a dispersion or suspension of said mixture of microparticles in a vehicle or carrier fluid in which they do not dissolve, optionally comprising a binding or viscosifying agent, (ii) applying said dispersion or suspension to one or more surfaces of the absorbable carrier, under atmospheric, reduced or elevated pressure, and optionally (iii), removing said vehicle.

Suitable processes for applying said dispersion or suspension to impregnate said carrier include percolation, spraying, dipping, soaking, dripping, impregnating, embedding, vacuum pressure impregnation, high pressure impregnation, and the like. Alternatively, a sandwich presentation may be formed by the application of the dispersion or suspension comprising a binding agent to the surface or surfaces of one or more separate carrier/matrices and adjoining them together before the optional removal of the vehicle or carrier fluid.

Suitable methods of removing said vehicle in step (iii) are well known to those skilled in the art but include, but are not limited to, air drying, freeze-drying, vacuum drying (optionally at elevated humidity), microwave vacuum drying, supercritical processing (such as RES, SEDS, etc.), forced air drying, and the like.

Suitable binding and/or viscosifying agents are known in the art, but most preferred such material include amphiphilic polymers such as hydropxypropyl cellulose, or PVP and the like. In this way, the suspension will demonstrate enhanced or adequate dispersion stability and thereby ensure a consistent dosing and homogeneity of application under step (ii) above, and maintain content uniformity within the composition.

In another preferred embodiment of the invention is provided a method of making a pharmaceutical composition comprising an absorbable carrier of a biocompatible, biodegradable polymer, and dispersed at least partially through, in or on said absorbable carrier, a mixture of first microparticles that comprise fibrinogen and/or second microparticles that comprise thrombin, optionally wherein either or both first and/or second microparticles further comprise a glassy carrier, wherein the absorbable carrier comprises a support material, such as a gauze, sponge, pad, bandage and the like, and the method includes the steps of; (i), forming a dispersion or homogenous suspension of said mixture of microparticles or blend thereof, in a vehicle or carrier fluid in which they do not dissolve, together with an appropriate amount of a biocompatible, biodegradable polymer in solution or suspension, optionally further comprising a binding or viscosifying agent, and (ii), removing said vehicle. In this way, a composite of the absorbable carrier comprising said mixture of microparticles is formed with said microparticles entrapped with, on or throughout said absorbable carrier. The method of removal of said vehicle or carrier liquid greatly influences the nature of the final composition obtained. For example, freeze-drying can result in a porous matrix of the biocompatible, biodegradable polymer and/or composition according to the invention, whereas simple air-drying can result in a film of said biocompatible, biodegradable polymer and/or composition according to the invention.

Suitable concentration ranges for the solution of the biocompatible, biodegradable polymer in such a freeze-drying process, may include about 0.1 to 70% w/v, or about 0.5 to 50% w/v, or about 0.75 to 10% w/v, or about 1 to 5% w/v. Suitable concentration ranges for the solution of the binder or viscosifying agent for use in methods of manufacturing compositions according to the invention, include about 0.001 to 50% w/v, or about 0.01 to 10% w/v, or about 0.1 to 5% w/v, or about 1 to 3% w/v.

Suitable methods of removing said vehicle in step (ii) are well known to those skilled in the art but include, but are not limited to, include air drying, freeze-drying, vacuum drying optionally at elevated humidity, microwave vacuum drying, supercritical processing (such as RES, SEDS, etc.), forced air drying, and the like. Preferably, the residual amount of vehicle, moisture content, carrier fluid, solvent or the like, is reduced to an acceptable or appropriate level.

The method of manufacture described above may be operated under sterile or aseptic conditions, so as to avoid the need for terminal sterilisation of the composition using gamma irradiation, electron-beam sterilisation, or treatment with ethylene oxide, or other such techniques known to those skilled in the art. Alternatively, such processes may be used and/or necessary when the method of manufacture is not operated under aseptic or sterile conditions.

As used herein, "moisture content" or "residual solvent" refers to the amount freely-available water or solvent or the like, in a composition according to the invention. "Freely-available" means the residue is not bound to or complexed with one or more of the non-liquid components of a composition according to the invention. The moisture content referenced herein refers to levels determined by procedures such as modified Karl Fischer method or by near infrared spectroscopy. Suitable moisture content(s) or residual solvent levels for a particular composition according to the invention may be determined empirically by one skilled in the art depending upon the intended application(s) thereof. For example, in certain embodiments of the present invention, higher moisture or solvent contents are associated with more flexible compositions according to the invention. Thus, in certain applications, it may be preferred to have a moisture content of at least about 3% to about 6% by weight or even in the range of about 6% to 44% by weight. In other embodiments of the present invention, lower moisture contents are associated with more rigid compositions. Thus, in applications for wounds to the abdomen or chest, for example, it may be preferred to have a moisture content of less than about 6% by weight or even in the range of about 1% to about 6% by weight of a composition according to the invention.

Thus, suitable ranges of moisture or residual solvent contents for compositions according to the invention include, but are not limited to, the following (each value being±0.9%): less than 53%; less than 44%; less than 28%; less than 24%; less than 16%; less than 12%; less than 6%; less than 5%; less than 4%; less than 3%; less than 2.5%; less than 2%; less than 1.4%; between 0 and 12%, non-inclusive; between 0 and 6%; between 0 and 4%; between 0 and 3%; between 0 and 2%; between 0 and 1%; between 1 and 16%; between 1 and 11%; between 1 and 8%; between 1 and 6%; between 1 and 4%; between 1 and 3%; between 1 and 2%; and between 2 and 4%, by weight of the composition.

In a further embodiment of the invention, the mixture of microparticles incorporated into compositions of the invention may be dispersed at least partially through, in or on said absorbable carrier at a concentration per unit area of the carrier ranging from about 1 mg of said mixture or homogenous blend thereof, per square cm, to about 5000 mg per square cm, or about from 10 mg per square cm to about 2000 mg per square cm, more suitably from about 25 mg per square cm to about 500 mg per square cm. Even more preferably, the mixture of microparticles is homogenously distributed and/or fixed through, in or on said absorbable carrier, preferably fixed on. With reference to the term "fixed" it is intended to mean that the microparticles are attached, glued, fused, embedded, dried in, on or through, or bound or in any other way and/or connected to the carrier such that they do not readily detach during transit and/or use. A suitable test for such fixation is one which determines the amount of microparticles removed after exposure of the composition of the invention to shaking or vibration. For examples, a relevant procedure is one such as that found in U.S. Pat. No. 7,052,713, wherein the assessment of the strength of fixation of microparticles to a carrier is such that abrasion of said composition is less than 1.0 mg/cm$^2$ when a sample of said composition is shaken on a Vibrofix shaker at a frequency of about 1000 rpm for 2 minutes Accordingly, compositions according to the invention, when subjected to the same test procedure, exhibit an abrasion of less than about 50 mg/cm$^2$, or less than about 40 mg/cm$^2$, or less than about 30 mg/cm$^2$, or less than about 20 mg/cm$^2$, or less than about 10 mg/cm$^2$, or even less than about 2 mg/cm$^2$.

In another preferred embodiment of the invention is provided a method of making a pharmaceutical composition comprising an absorbable carrier of a biocompatible, biodegradable polymer, and dispersed at least partially through, in or on said absorbable carrier, a mixture of first microparticles that comprise fibrinogen and/or second microparticles that comprise thrombin, optionally wherein either or both first and/or second microparticles further comprise a glassy carrier, wherein the absorbable carrier before and/or after incorporation of said mixture of microparticles, has a porosity or void fraction of between 1 and 99.9%, or about between 5 and 99%, or about between 10 and 98%, or about between 15 and 95%, wherein the porosity or void fraction is the fraction of the volume of voids over the total volume, expressed as a percentage. Alternatively, pores when present in the composition may have a diameter of from about 0.5 microns to about 5 mm, or from about 1 micron to about 1 mm or even from about 10 microns to about 500 microns.

In another preferred embodiment of the invention is provided a method of making a pharmaceutical composition comprising an absorbable carrier of a biocompatible, biodegradable polymer, and dispersed at least partially through, in or on said absorbable carrier, a mixture of first microparticles that comprise fibrinogen and/or second microparticles that comprise thrombin, optionally wherein either or both first and/or second microparticles further comprise a glassy carrier, wherein the composition demonstrates an absorption capacity to take up more than about 10, or about 20, or about 30, or about 40 or about 50 or even about 100 times or more, its own weight in blood or other body fluids. Such impregnated supports and sponges and the like allow the blood to seep into the structure before or whilst clotting occurs.

The marking of the treated support could take the form of imprinting the percentage strength, e.g., 20%, 40% or 60%, on the surface of the treated support (on one or both sides) or just underneath one layer thereof. The percentage markings may be any other preferred figures, such as 25%, 50% and 75%, or even 1, 2, 3, 4, 5, as desired. After the marking is done, the treated support is subjected to sterilization as desired.

The dimensions of the pharmaceutical composition may be any such size, area and volume as required for a particular application or bleeding rate and would be apparent to those skilled in the art. These may include 1×1 cm, 2×2 cm, 3×3 cm, and so forth. The thickness of the pad may be adapted for a particular application or bleeding rate and would be apparent to those skilled in the art, but may include between about 0.1 cm and 10 cm thick, or about 0.5 to 5 cm, for single or sandwich compositions.

Such novel presentations of the pharmaceutical compositions of the invention, exhibit synergy and/or greater efficacy compared to the microparticle components alone or a blend thereof, by encouraging clot formation at the interface of the wound and the composition where the dry powder microparticle components and/or blend thereof has been embedded and/or coated.

Other preferred methods of the invention are useful for sealing incisions, perforations, and/or fluid or gaseous leaks in biological tissues during a surgical procedure, and comprise contacting the tissue with a composition according to the invention, thereby sealing the incision, perforation, or fluid or gaseous leak.

EXAMPLES

Example 1

Dry powder fibrin sealant was prepared, as described in co-pending application U.S. Ser. No. 12/636,718. In brief, Fibrinogen (ZLB, Marburg, Germany) and trehalose-based (Pfanstiehl, Waukegan, Ill., USA) hollow spherical particles were prepared, as described in this application. The concentration of fibrinogen in the particles is 12% (w/w). Thrombin (SNBTS, Glasgow, Scotland) and trehalose were spray dried to obtain hollow particles. Thrombin was present in a concentration of 1000 IU per gram of particles. The particles were blended in a 1:1 ratio; the resulting powder has a 6% w/w concentration of fibrinogen and 500 IU/gram of powder. This blend is hereinafter referred to as Fibrocap®.

The Fibrocaps® powder is placed in an open aerosol can or bottle, the valve stem and top are placed thereon and crimped into place. The amount of added powder is approximately 1 to 1.5 grams. The propellant, in liquified form, then is filled into the aerosol container through the valve from a tank where it exists in liquified form. The aerosol is then applied to the wound by actuation of the valve to release the contents of the aerosol can, resulting in rapid hemostasis.

Example 2

The Fibrocaps® powder of Example 1 is admixed in a 1:1 ratio with PEG 200 and 0.5% Tween 80, to produce a light, liquid suspension and packaged in a bottle which is then to be applied to a wound, resulting in rapid hemostasis.

Example 3

The Fibrocaps® powder of Example 1 is admixed in a 1:1 ratio with PEG 800 to produce a paste and packaged in a tube which is then to be applied to a wound, resulting in rapid hemostasis.

Example 4

The present example describes how a product can be prepared in which both the active and passive hemostatic properties of Fibrocaps® powder, which consists of thrombin and fibrinogen in unreactive, spray-dried form (until contact with aqueous environment), may be retained in a "ready-to-use" sponge for application in moderate to severe bleeding indications. The Fibrocaps® is cast onto a passive hemostatic sponge as an active hemostasisor sealant layer or embedded throughout. In this example a Spongostan/Surgifoam (absorbable gelatin sponge USP) was used because its thickness may provide some benefit from both a Fibrocaps® casting and absorptive property perspective. It is also likely less costly and has more well-established history for use alone and in conjunction with thrombin solutions for comparisons.

The Fibrocaps® powder of Example 1 was first dispersed in ethanol-based casting solutions, applied drop-wise to cover the surface of a Spongostan absorbable gelatin sponge, and dried. Ethanol-based casting solutions containing the Fibrocaps® powders of Example 1 comprising several additives, including plasticizers (i.e. propylene glycol; PG, glycerol; G) and hydroxypropyl cellulose (i.e. HCP-LF, HPC-GF, HCP-HF) in combination, were evaluated for their effects on hemostatic sponge handling properties (i.e. flexibility, brittleness, stiffness, etc.), as well as functional properties (i.e. fluid absorption, adhesiveness to saturated gauze). FC embedded sponges were initially prepared and evaluated using various casting solution compositions with dispersions of 180 mg, 350 mg or 700 mg FC/3 mL/3.5×2.5×1 cm Spongostan. Hydroxypropyl cellulose (HPC) was added for its impact on retainment of Fibrocaps® within or on the surface of the sponge, as well as potentially adding bioadhesive properties to the product. Importantly, HPC is soluble in both ethanol and water. It is available in different viscosity grades. Lower viscosity grades (LF) may be more appropriate for application and subsequent penetration of the Fibrocaps® suspension, but the HF and GF grades can be used as viscosifying agents to enhance homogeneity of the Fibrocaps® suspension.

Propylene glycol and glycerol were added as co-solvents to render plasticizer properties upon the sponge surface (i.e. minimize brittleness/stiffness and to improve absorptive properties. They also protect the sponge to be modified in an undesirable way by exposure to organic solvents. For the test, briefly, a piece of 10×10 cm gauze was folded over twice, placed in a 60 cm Petri dish and 20 mL of TBS was added to saturate the gauze. One sponge representing each casting solution was placed over the TBS saturated gauze and light pressure was applied for 30 seconds. The relative absorptiveness of each sponge representing each casting solution was noted; it should be recognized that Spongostan absorbable gelatin sponge does not readily absorb aqueous solution unless pre-saturated by kneading. Each sponge representing each casting solution composition was allowed to set in contact with the TBS saturated gauze for 5 minutes and then the adhesiveness was assessed by attempting to lift/separate the sponge from the gauze.

A casting solution composed of 94% ethanol, 5% PG, and 1% HPC-LF gave good results; taking together the ease of preparation, dried sponge handling/absorptive properties, and the fibrin adhesiveness to TBS saturated gauze. While the results obtained are specific to the Spongostan absorbable gelatin sponge, they may be generally applied to other hemostatic sponges such as those based on collagen, chitosan, synthetic polymers, and hyaluronic acid, etc. Adherence to TBS saturated gauze was clearly improved with increasing FC loads in the range of 180 mg to 700 mg per 3.5×2.5×1 cm Spongostan sponge. This indicates that hemostasis efficacy in severe bleed indications may be improved with increasing FC loads.

It was observed that gelatin sponges without plasticizer also gave good results. Such sponges were tested in a severe bleeding model.

Example 5

This example assessed the hemostasis capacity of a Fibrocaps® loaded gelatin sponge which was prepared without the addition of plasticizer. Spongostan FC-FTP pads were basically prepared as follows:

- 98.8 grams of absolute Ethanol were weighed out in a glass Scotch bottle.
- 1.04 grams of HPC-LF were added.
- Solution was left stirring with a magnetic stirrer bar for 2 hrs at 37° C.
- 6 ml aliquots of this solution were added to 1.4 gram aliquots of irradiated FC and homogenized in a 15 ml falcon tube.
- 2800 mg of FC dispersed in 12 ml % (w/w) HPC-LF in EtOH, were evenly distributed over the surface of a 5×7×1 cm Spongostan pad dripping the entire volume of the suspension on one side of the pad.
- FC/HPC-LF coated pads were air dried overnight in a fume hood.

A Sponge to which No Fibrocaps® was Added, Served as a Control.

Domestic swine (Sus scrofa domestica) 50 kg or greater are sedated and placed on gas anesthesia. A small midline laparotomy incision is made to extend posteriorly from the tip of the sternum. The spleen is exposed and turned such that the splenic artery and vein are dorsal facing. To create the severe bleeding wound, a scalpel is used to cut a 30-40 mm gash in the spleen that transects both the exteriorized splenic vein and the splenic artery beneath the surface of the splenic tissue. The resulting wound is a highly pulsatile, bright red bleed indicative of arterial as well as tissue damage. Bleed rates are 30 to 60 g/min for slightly smaller wounds to over 120 g/min for larger wounds or wounds nearer to the anterior portion of the spleen. It can be anticipated that if either suture or a robust hemostatic intervention is not placed onto the wound to control the bleeding, that a drop in blood pressure and heart rate will ensue.

The results showed that hemostasis was achieved in two out of three trials using the 2800 mg Fibrocaps®/HPC Spongostan sponge. The control sponge did not lead to hemostasis and resque treatment was required.

Example 6

Preparation of Fibrocaps® Loaded Chitosan Pads

This Example describes the loading of Fibrocaps® powder onto a proprietary marketed chitosan pad (CoreLeader Bio, Taiwan), to produce a hemostatic composition according to the invention. The microparticles prepared in Example 1 were repeated for this experiment as follows; the spray-dried fibrinogen-containing microparticles had a particle size (×50, geometric diameter) of 18.4 μm and a fibrinogen content of 152 mg/g. The moisture content (Karl-Fischer) was 2%. The spray-dried thrombin-containing powder had a particle size (×50, geometric diameter) of 12.5 μm and a thrombin content of 977 IU/g. The moisture content (Karl-Fischer) was 3%. The two spray-dried powders were blended in a 1:1% w/w ratio using a drum mixer at 18 rpm for 15 minutes. The resultant blend had a particle size of 15.5 μm, and a fibrinogen content of 69.1 mg/g. The blend was then filled into glass vials at a 1.5 g fill mass and then irradiated to render them sterile.

A mass of 180 mg of the irradiated Fibrocaps® was suspended in 3 ml ethanol or in 3 ml ethanol containing 30 mg HPC-LF, resulting in a pad with a 24 mg/cm$^2$ Fibrocaps® loading. The FC powder dispersion was mixed well by repeated withdrawal and expulsion within a Pasteur pipette. The dispersion was applied drop-wise to the surface of a 3×2.5 cm section of Hemo-Pad (CoreLeader Bio); best efforts were made to evenly distribute the application over the surface. This was performed in duplicate yielding two loaded pads. Both pads were vacuum dried, coated side down on a 53 micron 30 cm Endecott sieve at 40° C. for 2 hours (the protocol stated 4 hours, however, it was noted that the pads were dry after 2 hours so they were removed from the oven early).

Following the same protocol, 350 mg of the irradiated Fibrocaps® was suspended in 3 ml ethanol or in 3 ml ethanol containing 30 mg HPC-LF, resulting in a pad with a 47 mg/cm² Fibrocaps loading.

Example 7

Characterisation of Loaded Chitosan Pads

The loaded pads prepared in Example 6 were evaluated for flexibility and adhesion.

Visual assessment showed that loadings with ethanol only gave inferior results compared to the loadings in which HPC-LF was also present. This was observed at both concentrations of loading. When ethanol only was used, this resulted in a thick layer of Fibrocaps® on the surface of the pad. This cake appeared cracked in several places. With the ethanol/HPC-LF mixture a thin layer of Fibrocaps® was present on top of the pad. This shows that ethanol/HPC-LF mixture can be used to load Fibrocaps® on a pad. In contrast to the ethanol only pads, the pads prepared with the ethanol/HPC-LF mixture were also easy to handle and still flexible without powder cracking or flaking.

The pads prepared using ethanol/HPC-LF and loaded with 24 mg/cm² and 47 mg/cm² Fibrocaps®, respectively were tested for adhesion, using the following methodology: A piece of 10×10 cm gauze (Boots Pharmaceuticals, UK) was folded over twice, placed in a 60 cm Petri dish and 20 mL of TBS (50 mM, pH 7.4) added to saturate the gauze. The loaded pad was placed over the TBS saturated gauze and light pressure applied for 30 seconds. The relative absorptiveness of each sponge observed with each casting solution was recorded. Each pad was allowed to set in contact with the TBS saturated gauze for 5 minutes. The adhesiveness was assessed by attempting to lift or separate the sponge from the gauze. After 30 seconds, for both type of pads adhesion to the gauze was observed. In both cases, the pad became very flexible and the top of the pad started to show absorption After 5 minutes, in both cases, the pad was very flexible, had a gel like appearance and there was still adhesion to the gauze. The adhesion of the pad loaded with 47 mg/cm² Fibrocaps® was stronger than the adhesion observed for the pad with a 24 mg/cm² load. These data demonstrate that loaded pads prepared using ethanol/HPC-LF were able to adhere and retain their flexibility. These pads were now tested for hemostasis in severe bleeding conditions.

Example 8

The efficacy of the chitosan-loaded pads produced in Example 6, was assessed in a severe bleed porcine injury model. A chitosan pad comprising no Fibrocaps® was used as a control, denoted placebo here.

In two pigs bleeding wounds were made by creating a laceration that cut across the smaller dorsal artery on the spleen and into the underlying vein and larger artery. These wounds were made using a scalpel to cut a roughly 2 cm wound across the vessels and adjacent tissue. This wound did not completely transect the organ, but was deep enough to cause profuse arterial bleeding requiring pressure and a hemostatic agent. Gauze pads were immediately applied to the cut to soak up the blood for approximately 30 seconds to determine the bleeding rate. The weight of blood collected was determined by weighing the blood soaked gauze pads and subtracting the dry weight of those pads to arrive at the weight in grams of blood absorbed and to determine bleeding rate. Treatment consisted of applying a hemostatic pad to the wound in a single layer with the Fibrocaps® layer (active treatments) oriented down toward the wound. Placebo pads had no Fibrocaps® coated onto them and therefore no particular orientation.

Both type of treatment pads were held in place with clean gauze pads and a timer started. After 3 minutes, the gauze pads were carefully lifted from the treatment pad to observe for hemostasis. In cases where there was no hemostasis at this 3 minute point, the treatment and direct pressure were reapplied for 3 minutes longer before another observation was made. If hemostasis was not achieved after a total of 6 minutes (failure), rescue was initiated using Ultrafoam, Fibrocaps® powder, and pressure, or a combination of these elements.

The results are presented in Table 1 and show that chitosan pads according to the invention are very effective in achieving hemostasis. A chitosan pad with a dose of 24 mg/cm² Fibrocaps® was able to achieve hemostasis in an extreme bleed of 184 g/min. Hemostasis was also observed with chitosan pads with 47 mg/cm² loading. They showed the strongest adherence to the wound, promoted hemostasis and had good handling properties.

TABLE 1

| Material | Findings Hemostasis (Yes/No) | Bleeding Rate (g/min) |
| --- | --- | --- |
| Chitosan + 47 mg/cm2 FC | Yes | 42 |
| Chitosan + 47 mg/cm2 FC | Yes | 58 |
| Chitosan + 47 mg/cm2 FC | Yes | 92 |
| Chitosan + 24 mg/cm2 FC | Yes | 184 |
| Chitosan CoreLeader Hemo-Pad + 0 mg FC (control) | No | 58 |

What is claimed is:

1. A pharmaceutical composition comprising an absorbable carrier of a biocompatible, biodegradable polymer and microparticles comprising fibrinogen in an amount of from about 0.1-15 mg/cm2 and/or microparticles comprising thrombin in an amount of from about 0.01 to 500 IU/cm2, wherein the microparticles further comprise a glassy carrier, and wherein the microparticles are homogeneously attached to said absorbable carrier.

2. The pharmaceutical composition according to claim 1, wherein the composition comprises a mixture of microparticles comprising fibrinogen and microparticles comprising thrombin.

3. The pharmaceutical composition according to claim 2, wherein the glassy carrier of the microparticles comprises trehalose.

4. The pharmaceutical composition according to claim 1, wherein the absorbable carrier is flexible or porous, and the composition optionally further comprises a plasticizer, binder or viscosifying agent.

5. The pharmaceutical composition according to claim 4, wherein the absorbable carrier is both flexible and porous.

6. The pharmaceutical composition according to claim 1 wherein the absorbable carrier comprises a biocompatible polymer selected from the group consisting of polysaccharides, albumin, a cellulose, methylcellulose, alkylhydroxyalkyl cellulose, hydroxyalkyl cellulose, cellulose sulfate, salts of carboxymethyl cellulose, carboxymethyl cellulose, carboxyethyl cellulose, oxidised cellulose; gelatins or collagen, such as a collagen-sponge, chitin, carboxymethyl chitin, hyaluronic acid, salts of hyaluronic acid, alginate, alginic acid, propylene glycol alginate, glycogen, dextran, dextran sulfate, curdlan, pectin, pullulan, xanthan, chondroitin, chondroitin sulfates, carboxymethyl dextran, heparin, heparin sulfate, heparan, heparan sulfate, dermatan sulfate, keratan sulfate, carrageenans, starch, amylose, amylopectin, poly-N-glucosamine, poly-N-acetyl glucosamine, polymannuronic acid, polyglucuronic acid, polyguluronic acid; chitosan, chitin, chitin-glucan, chitosan-glucan, carboxymethyl chitosan, chitosan salts, chitosan derivatives thereof, and any combinations thereof; a polyurethane, oxidised polysaccharides, and derivatives or combinations of any of the above.

7. The pharmaceutical composition according to claim 1, wherein the composition is provided as a dry adhesive coating, aerosol, dry aerosol, pump spray, medical compress; film; coated plaster; medicated sponge or surgical patch, hemostatic fleece; hemostatic pad; gauze; salve, semigel, gel, foam, paste, suspension, ointment, emulsion, moldable form, nasal plug, surgical dressing, wound packing, bandage, swab, catheter, fibre optic, syringe, pessary, suppository, or suspension in a liquid or non-aqueous liquid.

8. The pharmaceutical composition according to claim 6, wherein the absorbable carrier comprises chitosan, or derivative or salt or co-polymer thereof; gelatin, collagen or a polyurethane.

9. The pharmaceutical composition according to claim 1 wherein the fibrinogen or thrombin are recombinant, human, purified from a natural source, or transgenic.

10. The pharmaceutical composition according to claim 1 for hemostasis, tissue sealing or tissue gluing.

11. A method of treating a wound or reducing bleeding at a haemorrhaging site, comprising administering to the wound or haemorrhaging site a pharmaceutical composition according to claim 1.

12. The method according to claim 11, wherein said treatment results in a time to hemostasis of less than about 10 minutes when administered to a wound or haemorrhaging site which exhibits a bleeding rate of greater than about 30 g/minute.

13. The method according to claim 11, wherein the absorbable carrier consists essentially of a biocompatible, biodegradable polymer selected from a cellulose, polyurethane, gelatin or collagen, such as a collagen-sponge, or a chitosan, and amorphous fibrinogen or amorphous thrombin, and the treatment is for tissue sealing, tissue gluing or hemostasis.

14. The method according to claim 13, wherein the amorphous fibrinogen or amorphous thrombin exhibit a degree of crystallinity of at most about 10% by weight of the microparticle population in the carrier.

15. The method according to claim 13 wherein the treatment is for the topical treatment of a wound, and the wound is selected from the group consisting of a) minor abrasions, cuts, scrapes, scratches, burns, sunburns, ulcers, internal venous bleeding, external venous bleeding, and b) surgical interventions selected from gastrointestinal surgery, surgery on parenchymal organs; surgical interventions in the ear, nose and throat area (ENT), cardiovascular surgery, aesthetic surgery, spinal surgery, neurological surgery; lymphatic, biliary, and cerebrospinal (CSF) fistulae, air leakages during thoracic and pulmonary surgery, thoracic surgery, orthopaedic surgery; gynaecological surgical procedures; vascular surgery and emergency surgery, liver resection, and soft tissue injury or surgery.

16. The method according to claim 15, wherein the pharmaceutical composition is topically applied to a traumatic injury in the battle field, a wound or during or after surgery.

17. The pharmaceutical composition according to claim 9, wherein the recombinant fibrinogen is HMW fibrinogen or alpha-extended fibrinogen.

18. A pharmaceutical composition comprising:
an absorbable carrier comprising a biocompatible, biodegradable polymer; and
microparticles comprising fibrinogen in an amount of from about 0.1-15 mg/cm$^2$ and/or microparticles comprising thrombin in an amount of from about 0.01 to 500 IU/cm$^2$ attached in a homogenous distribution to said absorbable carrier,
wherein the microparticles further comprise a glassy carrier.

19. A pharmaceutical composition comprising: an absorbable carrier comprising a biocompatible, biodegradable polymer; and microparticles comprising fibrinogen in an amount of from about 0.1-15 mg/cm2 and microparticles comprising thrombin in an amount of from about 0.01 to 500 IU/cm2 homogeneously attached to said absorbable carrier, wherein the microparticles further comprise trehalose.

* * * * *